United States Patent [19]
Iizuka et al.

[11] Patent Number: 5,671,154
[45] Date of Patent: Sep. 23, 1997

[54] SIGNAL PROCESSING METHOD AND SIGNAL PROCESSING DEVICE FOR ULTRASONIC INSPECTION APPARATUS

[75] Inventors: Yukinori Iizuka; Hidekazu Horigome; Akira Murayama; Shin Nakazawa, all of Tokyo, Japan

[73] Assignee: NKK Corporation, Tokyo, Japan

[21] Appl. No.: 374,777

[22] PCT Filed: Jun. 7, 1994

[86] PCT No.: PCT/JP94/00916

§ 371 Date: Jan. 26, 1995

§ 102(e) Date: Jan. 26, 1995

[87] PCT Pub. No.: WO94/29714

PCT Pub. Date: Dec. 22, 1994

[30] Foreign Application Priority Data

Jun. 7, 1993 [JP] Japan ................. 5-135562

[51] Int. Cl.⁶ ................. G01N 29/04; G01N 29/10
[52] U.S. Cl. ................. 364/507; 73/600; 73/602; 73/609; 73/610; 73/614; 364/506; 364/551.01; 364/572; 364/574
[58] Field of Search ................. 73/592, 599, 600, 73/602, 609, 610, 611, 613, 614, 615, 632, 634; 364/506, 507, 550, 551.01, 572, 574, 575

[56] References Cited

U.S. PATENT DOCUMENTS

| | | | |
|---|---|---|---|
| 3,446,949 | 5/1969 | Trimble | 364/574 |
| 3,506,813 | 4/1970 | Trimble | 364/574 |
| 3,942,358 | 3/1976 | Pies | 73/611 |
| 4,435,984 | 3/1984 | Gruber | 73/628 |
| 4,470,304 | 9/1984 | Nusbieckel, Jr. et al. | 73/611 |
| 4,495,587 | 1/1985 | Plante et al. | 364/507 |
| 4,817,016 | 3/1989 | Thompson et al. | 364/507 |
| 4,869,109 | 9/1989 | Miglianico et al. | 73/602 |
| 4,928,182 | 5/1990 | Guerinot et al. | 348/818 |
| 5,163,323 | 11/1992 | Davidson | 73/290 V |
| 5,260,801 | 11/1993 | Temma et al. | 386/122 |
| 5,303,061 | 4/1994 | Matsumoto et al. | 386/13 |
| 5,497,662 | 3/1996 | Dykes | 73/634 |
| 5,511,425 | 4/1996 | Kleinert et al. | 73/627 |

FOREIGN PATENT DOCUMENTS

| | | |
|---|---|---|
| 0119844 | 9/1984 | European Pat. Off. . |
| 60-14165 | 1/1985 | Japan . |
| 61-162747 | 7/1986 | Japan . |

*Primary Examiner*—Edward Cosimano
*Attorney, Agent, or Firm*—Frishauf, Holtz, Goodman, Langer & Chick

[57] ABSTRACT

In an ultrasonic inspection apparatus for detecting a flaw present in a target object (2) on the basis of an echo signal (b) from the target object (2), a high-frequency echo signal (b) output from an ultrasonic transmit-receive unit (1) is A/D-converted at a high sampling frequency ($f_S$) in only a predetermined measurement time interval ($T_M$) in a repetitive period ($T_O$) of an ultrasonic pulse (a) and is temporarily stored in a storage unit (12). Thereafter, the sampling data is read out at a read frequency ($f_R$) lower than the sampling frequency ($f_S$). A digital signal process for noise reduction using a first digital filter (18) or a synchronous adding/averaging circuit (27) is performed to only data in the measurement time interval ($T_M$). As a result, noise included in the echo signal (b) is considerably reduced while on-line inspection is kept performed.

21 Claims, 21 Drawing Sheets

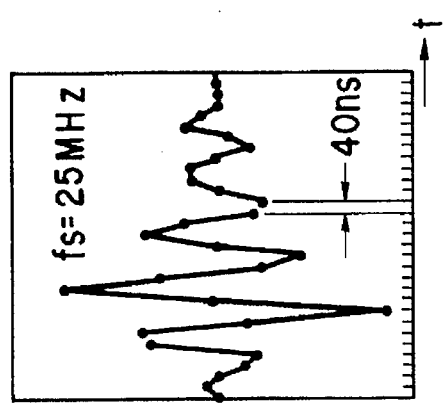
F I G. 4A
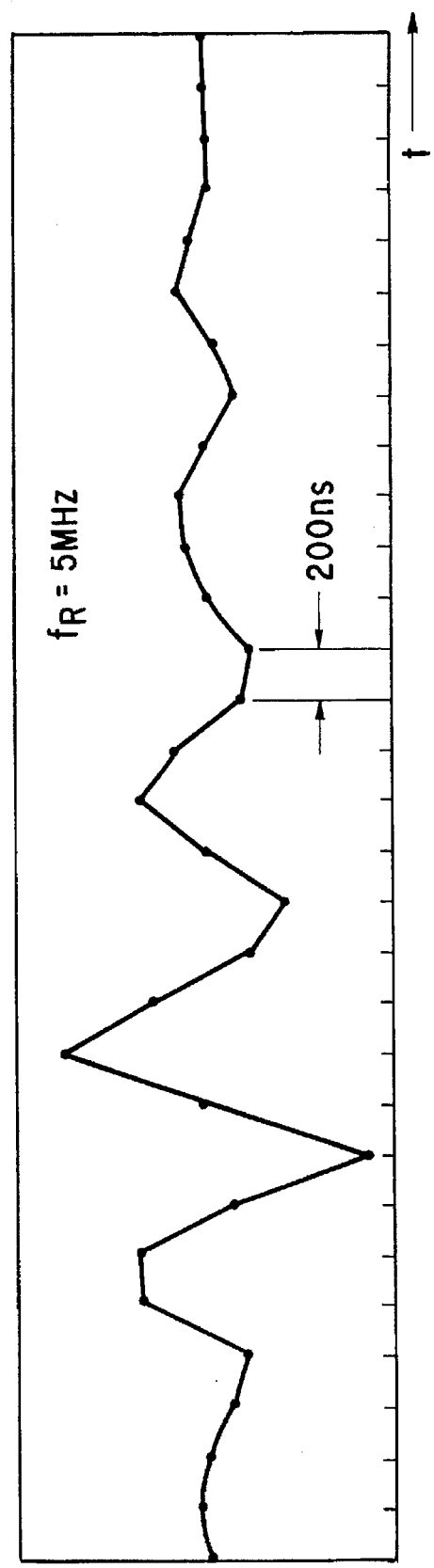
F I G. 4B

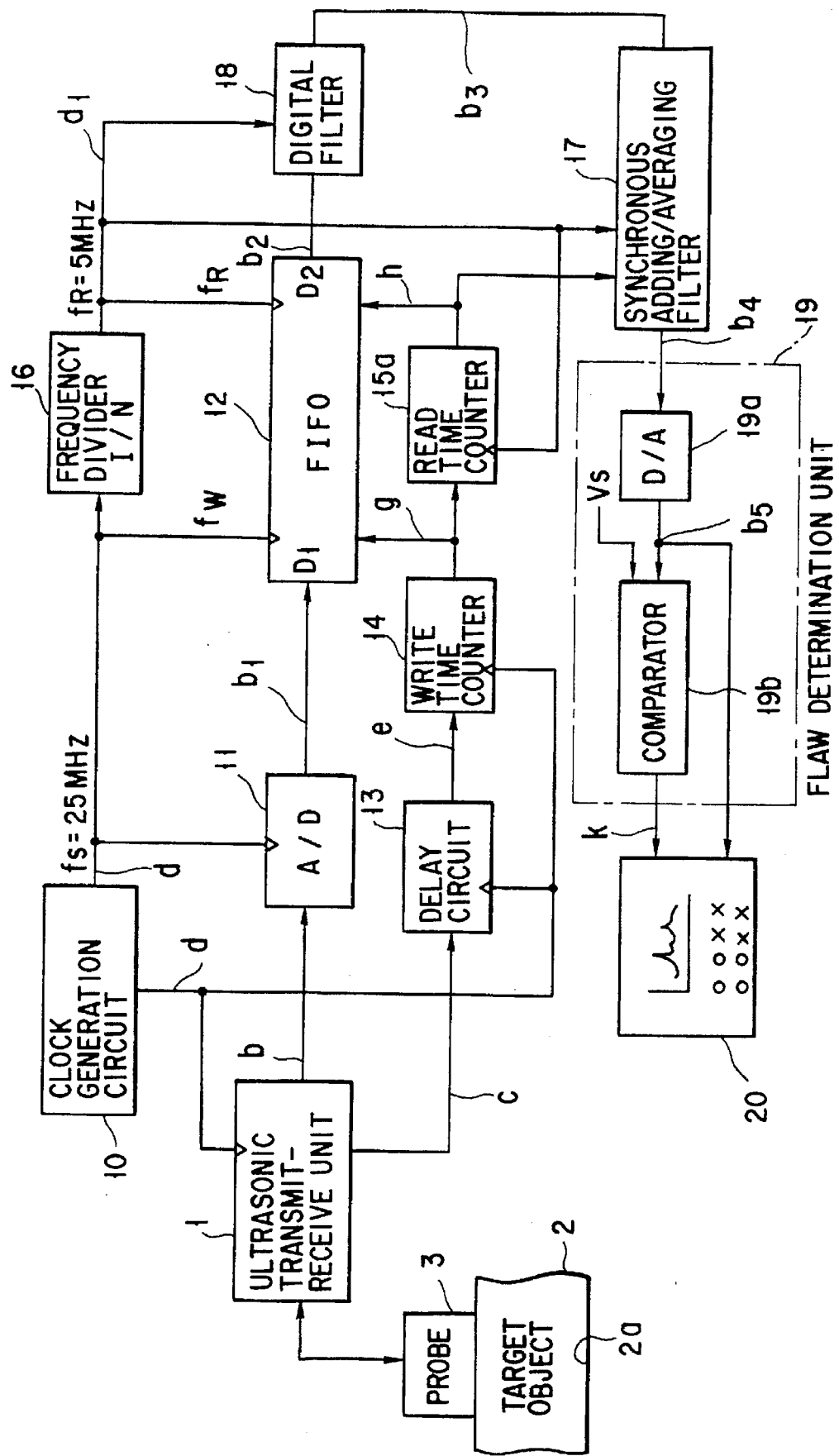
F I G. 5

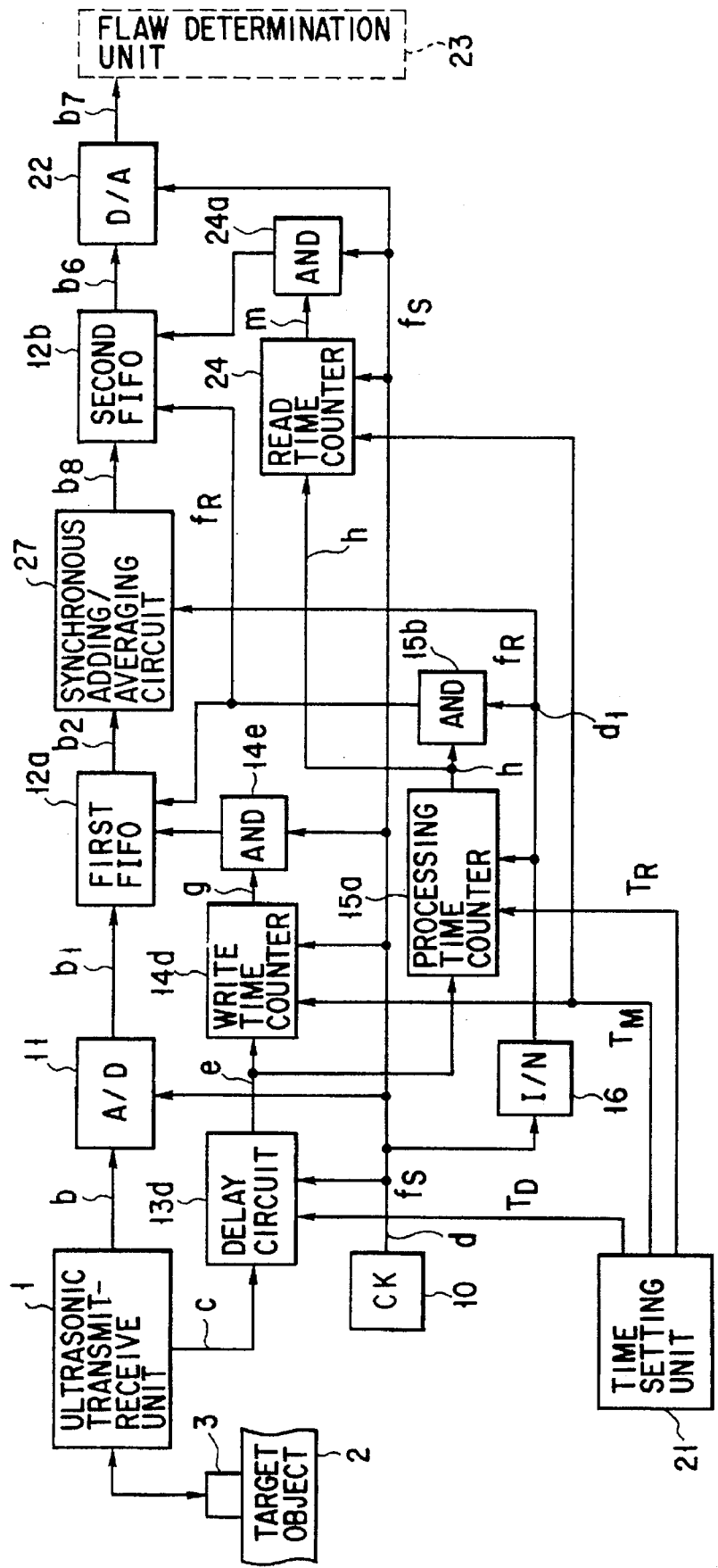
F I G. 14

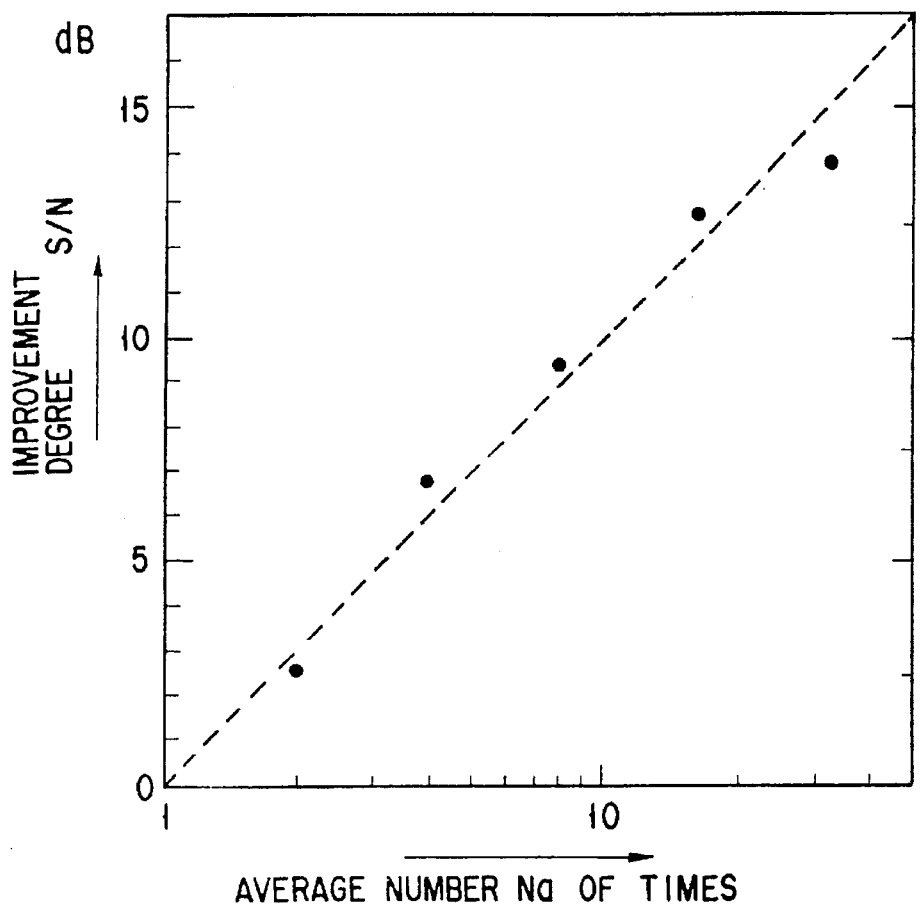
F I G. 17
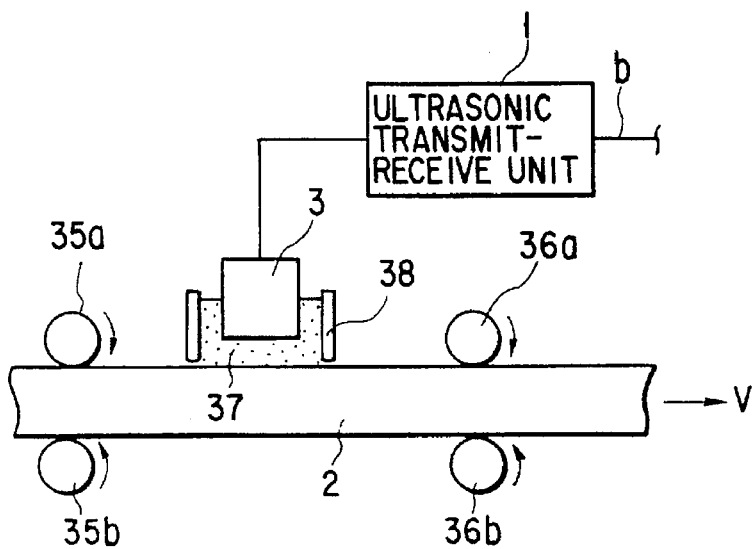
F I G. 18

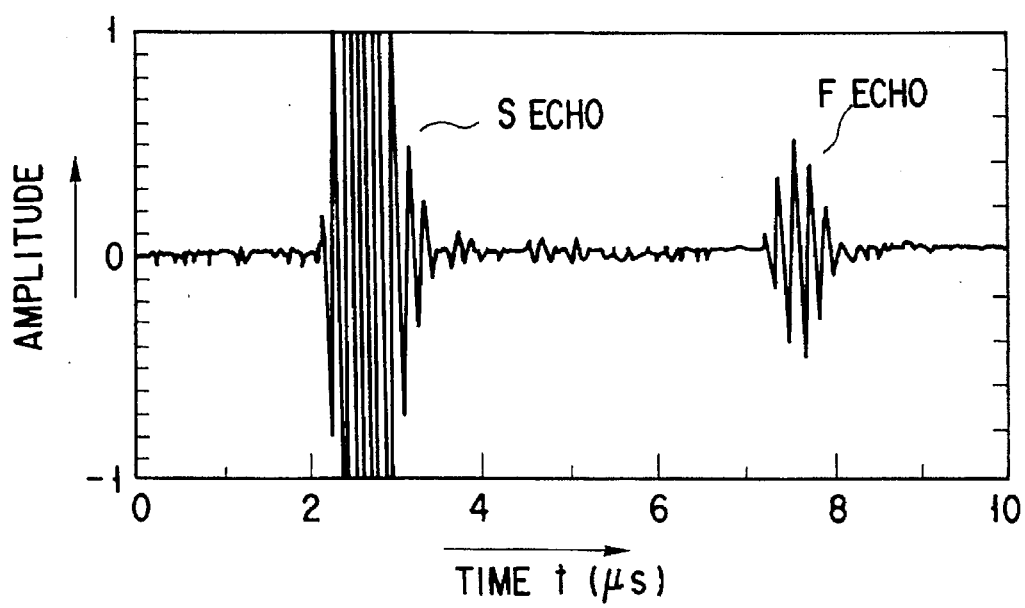
F I G. 21
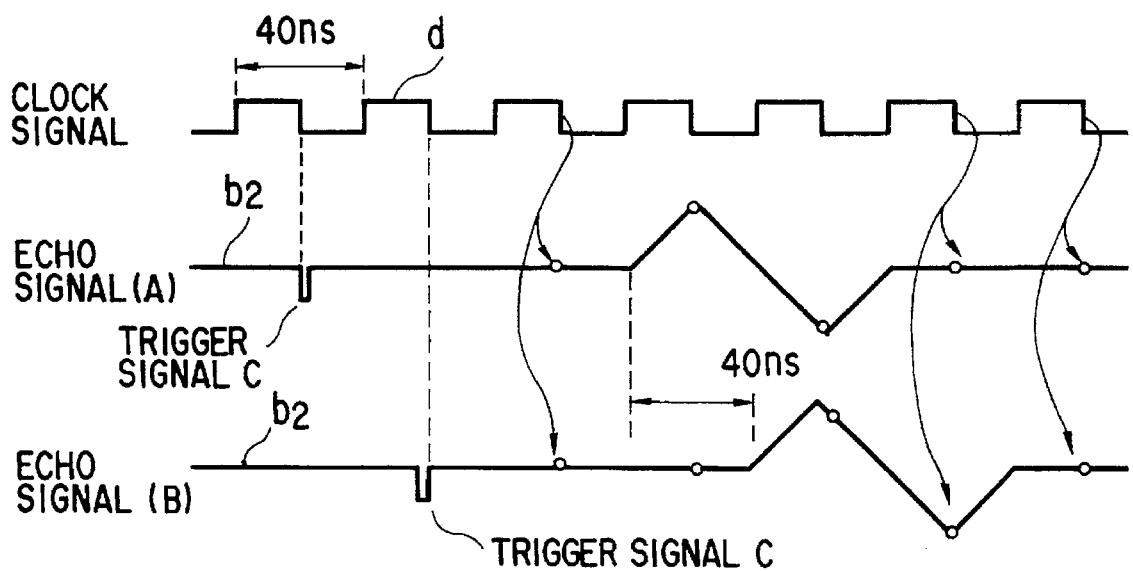
F I G. 24

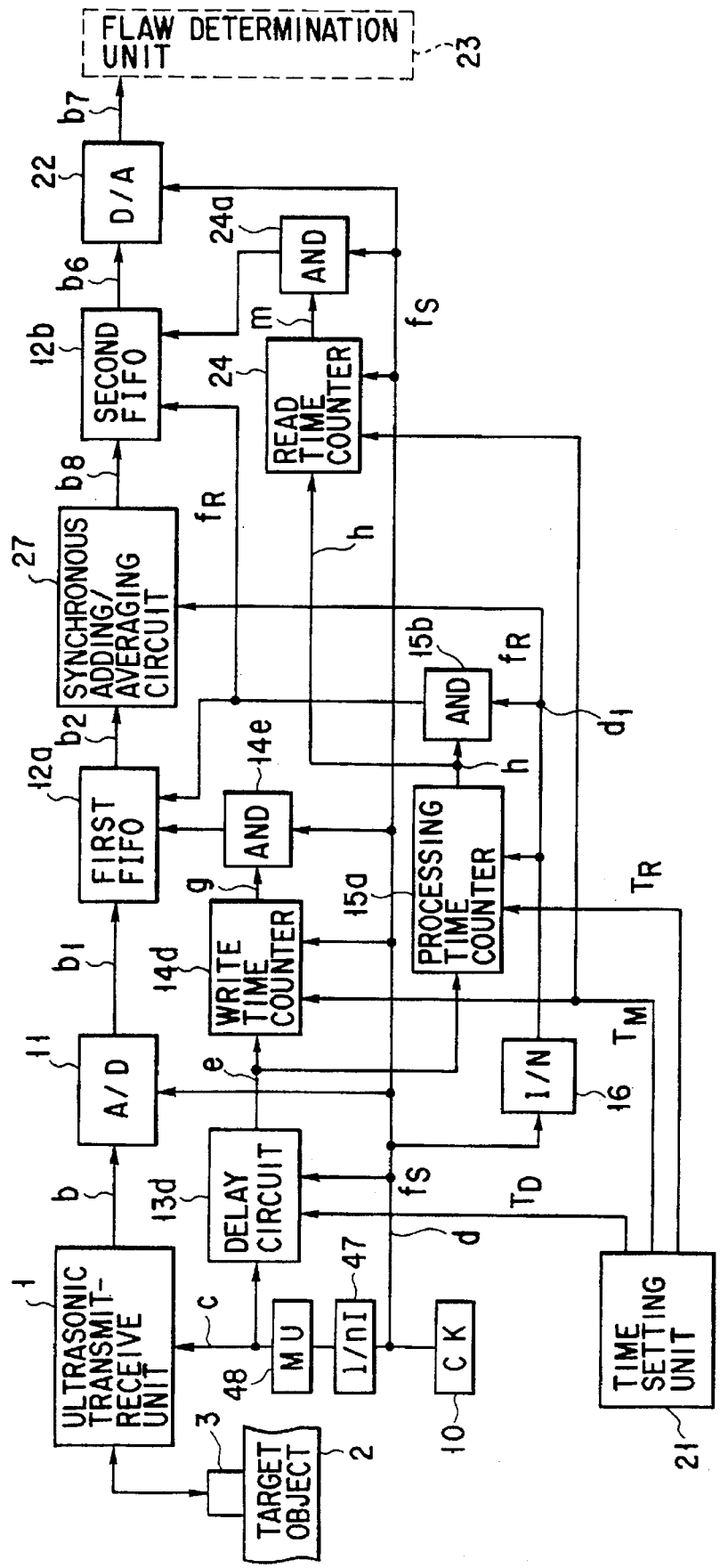
F I G. 23

SIGNAL PROCESSING METHOD AND SIGNAL PROCESSING DEVICE FOR ULTRASONIC INSPECTION APPARATUS

[TECHNICAL FIELD]

The present invention relates to an ultrasonic inspection apparatus which transmits an ultrasonic pulse to a target object and analyzes an echo signal detected from the target object to detect a flaw present in the target object and, more particularly, to a signal processing method and signal processing device in which, after a detected high-frequency echo signal is temporarily converted into a digital signal, noise of the digital signal is reduced.

[PRIOR ART]

An ultrasonic inspection apparatus is arranged as shown in FIG. 25. An ultrasonic transmit-receive unit 1 transmits a pulse signal at a predetermined period $T_0$ to a probe 3 provided to a target object 2 such as steel material directly or through a delay material such as water. As shown in FIG. 26, the probe 3 converts the received pulse signal into an ultrasonic pulse a to apply the ultrasonic pulse a to the target object 2. The ultrasonic pulse a applied into the target object 2 is reflected by a bottom surface 2a of the target object 2 and received by the probe 3 again. The probe 3 converts the reflected wave into an electrical signal to transmit the electrical signal to the ultrasonic transmit-receive unit 1. The ultrasonic transmit-receive unit 1 amplifies the electrical signal and transmits the amplified signal to a signal processing device 4 as an echo signal b.

The echo signal b includes a bottom surface (B) echo $5b$ corresponding to the wave reflected by the bottom surface $2a$ and a flaw (F) echo $5b$ caused by a flaw. In addition, a frequency f of the ultrasonic pulse a is determined by the thickness or the like of an ultrasonic vibrator incorporated in the probe 3. The frequency f of the ultrasonic pulse a used for inspection is set to be several MHz to ten and several MHz. Therefore, the frequency range of the signal waveforms of the bottom surface echo $5a$ and the flaw echo $5b$ included in the echo signal b is a wide range of 0 Hz to ten and several MHz.

The signal processing device 4 performs various signal processes to the echo signal b received from the ultrasonic transmit-receive unit 1, and the signal processing device 4 displays a signal process result and the presence/absence of a flaw on a display unit 6. In this case, in order to perform a signal process to the echo signal and display the echo signal, a trigger signal S synchronized with the pulse signal is supplied from the ultrasonic transmit-receive unit 1 to the signal processing device 4.

In the flaw inspection apparatus arranged described above, the echo signal a output from the ultrasonic transmit-receive unit 1 includes, in addition to the bottom surface echo $5a$ and the flaw echo $5b$, a larger amount of noise. When an amount of noise included in the ultrasonic pulse a is large, the reliability of an inspection result is considerably degraded. The noise is roughly classified into electrical noise and material noise.

The electrical noise is constituted by external noise caused by mixing an electromagnetic wave into the probe 3, the ultrasonic transmit-receive unit 1, a connection cable, or the like and internal noise generated by an amplifier or the like incorporated in the ultrasonic transmit-receive unit 1.

An ultrasonic wave propagating in the target object 2 is scattered by the crystal grain boundary of a material. This scattered ultrasonic wave is received by the probe 3. The echo signal b output from the probe 3 includes the received scattered ultrasonic wave as a scattered echo. This scattered echo is the material noise described above.

Reduction of the noise included in the echo signal b is very important to perform ultrasonic inspection at high accuracy.

Conventionally, an analog filter is used to reduce noise components included in the echo signal b. For example, a BPF (Bandpass Filter) for causing the frequency component of the ultrasonic echo to pass is used for electrical noise having a wide-frequency component. In addition, an LPF (Low-Pass Filter) or a BPF is used for material noise utilizing that the frequency distribution of the flaw echo $5b$ is lower than that of a scattered echo. In this manner, when an analog filter is used, noise components included in the echo signal b can be reduced to a level equal to or lower than a predetermined level.

It is generally known that the frequency distribution of a flaw echo changes by the ultrasonic attenuation characteristics of the target object 2. Therefore, when a BPF is to be used for material noise represented by a scattered echo or the like, a filter having optimal characteristics is desirably used in accordance with the target object 2. However, since the passing frequency characteristics of the analog filter cannot be easily changed, a large number of filters respectively having passing frequency characteristics corresponding to the ultrasonic attenuation characteristics of the materials of target objects 2 must be prepared. In this manner, when different filters are used in accordance with the material characteristics of the target objects 2, difficulties practically occur in consideration of operability or economic advantages.

In order to eliminate the above inconvenience, a digital signal processing technique is proposed. More specifically, the echo signal b output from the ultrasonic transmit-receive unit 1 is A/D-converted. A digital filter is used for the echo signal which is converted into a digital signal to remove a noise component.

For example, an FIR (Finite-Impulse Response) digital filter can freely change its passing characteristics. For this reason, when the passing frequency characteristics corresponding to the material of the target object 2 are set, a noise reduction process optimal for the echo signal b can be performed.

A sample calculation for a signal processing operation speed using this method is performed. For example, in order to perform a 128th order FIR digital filter process with respect to data at 1,024 points, the sum of products must be performed 128×1,024 times. Assuming that the sum of products is calculated once by five instruction steps, (128× 1,024×5) instruction steps are required. Therefore, if a general computer having a speed of about 40 MIPS is used, a time of $128 \times 1,024 \times 5/(40 \times 10^6)$=about 16 ms is required. In practice, since a time for data transfer between a memory and a CPU is added to the above time, an extra time is further required.

In addition, in a steel mill or the like, on-line inspection for performing inspection to the moving target object 2 such as a steel plate is performed. In this case, a portion to be inspected in the target object 2 is a portion on which the ultrasonic pulse a is incident. For this reason, when a repetitive period $T_0$ of the ultrasonic pulse a is long, the entire surface of the target object 2 cannot be inspected. For this reason, the repetitive period $T_0$ of the ultrasonic pulse a is generally set to be shorter than 1 ms. In order to perform the digital signal process to the echo signal b, a signal processing operation must be ended within a time of 1 ms which is the repetitive period $T_O$ of the ultrasonic pulse a.

In order to perform the digital signal process in a stage in which the ultrasonic pulse a has the above high frequency of several MHz to ten and several MHz, this high-frequency echo signal b must be directly A/D-converted. Since the echo signal b has a wide frequency distribution of 0 Hz to ten and several MHz, according to a sampling theorem, A/D conversion must be performed at a sampling frequency $f_S$ of at least 20 MHz or more. In addition, an operation process must be performed to sampling data sequentially formed at the high sampling frequency $f_S$.

In order to satisfy two conditions related to the above digital signal process described above, a high-speed computer having an operation speed of about 1,000 MIPS is required. Since such a system is very expensive, the system cannot be actually incorporated in an actual ultrasonic inspection apparatus.

An operation element capable of continuously performing a processing operation to a digital signal may be utilized. In this case, the digital signal is input/output at a timing equal to the period of the sampling period of the operation element, and a signal processing operation is continuously performed. For this reason, an operation time does not become longer than the repetitive period $T_O$ of the ultrasonic pulse a.

However, a digital filter operation element operated at a speed of the sampling frequency $f_S=20$ MHz or more is not realized at present.

For this reason, in an on-line ultrasonic inspection apparatus which must be operated under the condition in which the repetitive period $T_O$ of the ultrasonic pulse a is 1 ms or less, a digital signal process cannot be easily performed to an echo signal.

In addition, in general, in ultrasonic inspection, bristle echo caused by reflection from the crystal grain boundary of the above target object material is generated. As shown in FIG. 19, the pulse width of a surface echo (S echo) reflected by the surface of the target object increases. Echoes such as bristle echo or an echo occurring near the surface echo are not echoes caused by a flaw, and are called false echoes.

As a measure for reducing this false echo, a method in which a false echo is removed, using a frequency filter, from an echo signal obtained by causing an ultrasonic pulse having a large bandwidth to be incident on a target object is proposed (Jpn. Pat. Appln. KOKAI Publication No. 2-186261). This method utilizes that the frequency of a flaw echo is lower than the frequency of bristle echo.

However, depending on a target object material, the frequency of grass is not greatly different from the frequency of a flaw echo, and grass may not be completely removed by the frequency discrimination method including the digital filter. In addition, with respect to a false echo near a surface echo, the frequency of this false echo is basically equal to the frequency of the flaw echo. For this reason, as in the case of bristle echo, the false echo cannot be removed by the frequency filter. That is, there is no technique of effectively removing the false echo.

[SUMMARY OF THE INVENTION]

It is the first object of the present invention to provide a signal processing method and a signal processing device for an ultrasonic inspection apparatus capable of performing a digital signal process to an echo signal to reduce noise while a repetitive period of an ultrasonic pulse is kept short.

It is the second object, in addition to the above object, to provide a signal processing device of an ultrasonic inspection apparatus capable of effectively removing a false echo, reliably reducing small noise and expected noise, and more improving flaw-detection accuracy.

In order to achieve the first object, in the present invention, a high-frequency echo signal output from an ultrasonic transmit-receive unit for receiving a reflected wave from a target object is converted into a digital signal at a predetermined sampling frequency, and a measurement time interval in a repetitive period of an ultrasonic pulse is designated. Sampling data, in the measurement time interval, of the echo signal converted into the digital signal are sequentially stored at a write frequency equal to the sampling frequency, and the stored sampling data are sequentially read out at a read frequency lower than the write frequency. A digital filter performs a frequency discrimination process to the sequentially readout echo signals, and the presence/absence of a flaw is determined on the basis of the echo signal to which the frequency discrimination process is performed.

The operation principle of the present invention arranged as described above will be described below.

As described above, in order to perform on-line inspection, a repetitive period $T_O$ of an ultrasonic pulse a must be set to be several ms or less. In a high-frequency echo signal b output from the ultrasonic transmit-receive unit, a measurement time interval $T_M$ required for actually determining a flaw is a time from transmission time of the ultrasonic pulse a to time when a bottom echo is incident, and is several tens μs at most. This measurement time interval $T_M$ is considerably shorter than the repetitive period $T_O$ of the ultrasonic pulse a ($T_M < T_O$).

The echo signal b in the measurement time interval $T_M$ is A/D-converted into a digital signal at a high sampling frequency $f_S$. Of sampling data constituting the echo signal converted into the digital signal, each sampling data which is set within the measurement time interval $T_M$ is stored, using a write frequency $f_W$ equal to the sampling frequency $f_S$, in a storage unit constituted by, e.g., a FIFO (First-In First-Out) register. The sampling data stored in this storage unit are sequentially read out at a frequency lower than the write frequency $f_W$, i.e., at a read frequency $f_R$ at which the next digital filter can satisfactorily perform a data process.

A frequency discrimination process is performed to the readout digital echo signal with frequency characteristics which maximally effectively attenuate noise in the next digital filter. Therefore, a noise component included in the digital echo signal passing through this digital filter is considerably reduced. The presence/absence of a flaw is determined on the basis of the echo signal whose noise component is reduced.

In this case, the number $N_M$ of sampling data of an echo signal stored in the storage unit such as a FIFO register is the number of data present in the measurement time interval $T_M$. For this reason, a time $T_R$ required for reading out all the $N_M$ sampling data stored in the storage unit is represented by equation (1).

$$T_R = T_M(f_S/f_R) \qquad (1)$$

Assume that a time obtained by adding this read time $T_R$ and the measurement time interval $T_M$ is shorter than the repetitive period $T_O$ of the ultrasonic pulse. In this case, when the next period $T_O$ is started, succeeding sampling data is not left in the FIFO register.

Therefore, the digital filter performs need only perform a process to digital data sequentially output at the read frequency $f_R$ lower than the sampling frequency $f_S$. In addition, the number $N_M$ of digital data to which an operation process must be performed in the repetitive period $T_0$ of one ultrasonic pulse a is considerably smaller than the number of digital data present in all the time intervals of a repetitive period $T_0$ in the echo signal b. For this reason, the digital data can be satisfactorily processed within the repetitive period $T_0$.

More specifically, a high-performance digital filter capable of performing a special high-speed process need not be used as a digital filter.

In order to achieve the second object, in the present invention, a synchronous adding/averaging filter other than the digital filter in the signal processing device having the above arrangement is used. In addition, a synchronous adding/averaging circuit is used in place of a digital filter.

When the synchronous adding/averaging filter is used, an echo signal can be averaged every repetitive period $T_0$ of each ultrasonic pulse a, and noise reduction efficiency can be much improved. In this case, as in the case of a digital filter, a high-performance filter capable of performing a special high-speed process need not be used.

The synchronous adding/averaging circuit used in place of a digital filter, like the above synchronous adding/averaging filter, has a function of averaging a digital echo signal in the measurement time interval $T_M$. Noise components included in each echo signal respectively have different phases. For this reason, when a large number of echo signals are added to each other and averaged, the noise components are canceled, and the noise components are reduced as a whole. Therefore, the S/N of a flaw echo included in the echo signal increases.

[BRIEF DESCRIPTION OF THE DRAWINGS]

FIG. 4A is a waveform chart of an echo signal to be input to a FIFO register of the device of the embodiment in FIG. 1;

FIG. 4B is a waveform chart of an echo signal output from the FIFO register of the device of the embodiment in FIG. 1;

FIG. 5 is a block diagram showing the schematic arrangement of an ultrasonic inspection apparatus in which a signal processing device of another embodiment of the present invention is incorporated;

FIG. 14 is a block diagram showing the schematic arrangement of an ultrasonic inspection apparatus in which a signal processing device of still another embodiment is incorporated;

FIG. 17 is graph showing the relationship between an average number Na of times and an S/N showing the effect of the device of the embodiment in FIG. 14;

FIG. 18 is a view showing a main part extracted from a signal processing device of an ultrasonic inspection apparatus of still another embodiment;

FIG. 21 is a waveform chart of an echo signal whose false echo is reduced by the device of the embodiment in FIG. 18;

FIG. 23 is a block diagram showing the schematic arrangement of an ultrasonic inspection apparatus in which a signal processing device of still another embodiment is incorporated;

FIG. 24 is a timing chart for explaining the effect of the device of the embodiment in FIG. 23;

[BEST MODE OF CARRYING OUT THE INVENTION]

An embodiment of the present invention will be described below with reference to the accompanying drawings.

Figure 1:
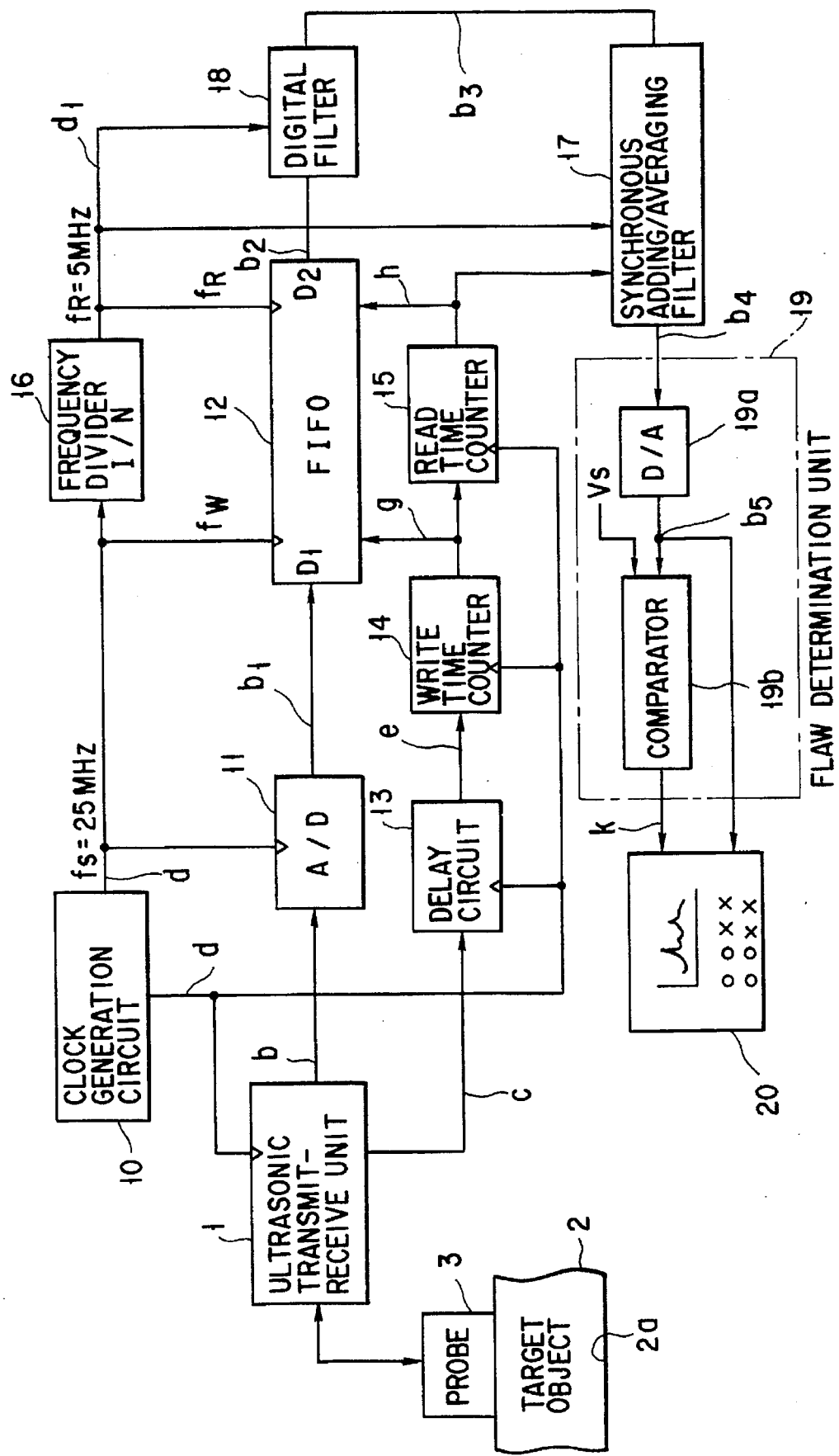
FIG. 1 is a block diagram showing the schematic arrangement of an ultrasonic inspection apparatus in which a signal processing device according to an embodiment of the present invention is incorporated.
Figure 25:
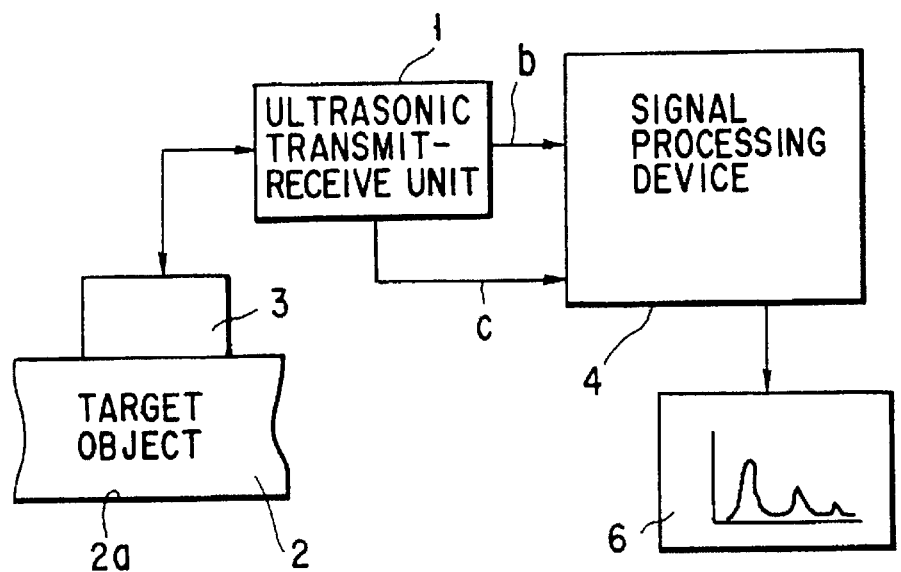
FIG. 25 is a view showing the schematic arrangement of a general ultrasonic inspection apparatus.
Figure 26:
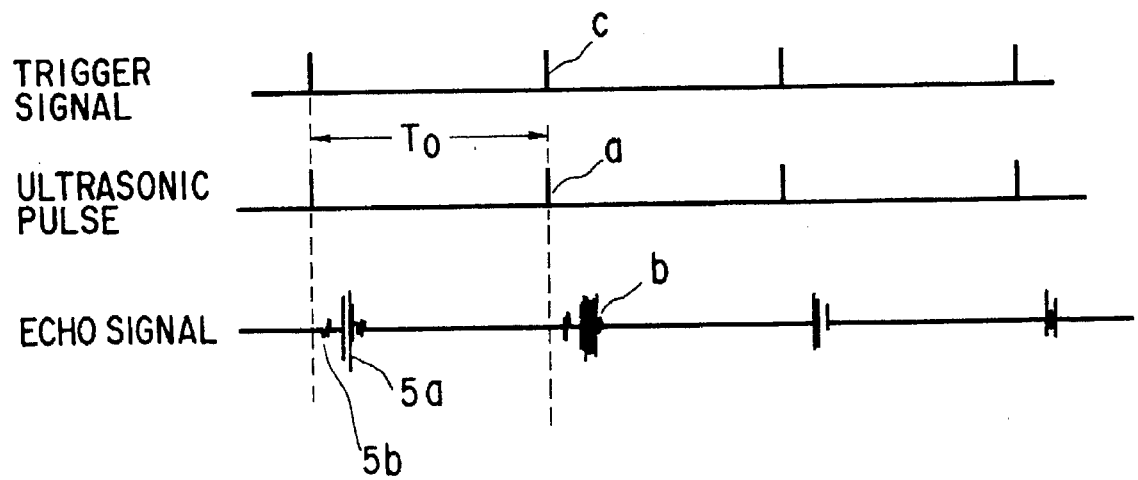
FIG. 26 is a timing chart showing the operation of the ultrasonic inspection apparatus in FIG. 25.

FIG. 1 is a block diagram showing an overall ultrasonic inspection apparatus in which a signal processing device of the embodiment is incorporated. The same reference numerals as in the ultrasonic inspection apparatus shown in FIG. 25 denote the same parts in FIG. 1. Therefore, a detailed description of the overlapping parts will be omitted.

A clock signal generation circuit 10 outputs a clock signal d having, e.g., a frequency $f_S$=25 MHz. The clock signal d output from the clock signal generation circuit 10 is applied to an ultrasonic transmit-receive unit 1. In addition, this clock signal d is also transmitted to an A/D converter 11, a FIFO register 12, a delay circuit 13, a write time counter 14, a read time counter 15, and a frequency divider 16.

The ultrasonic transmit-receive unit 1 frequency-divides the input clock signal d and transmits a pulse signal every predetermined period $T_0$ to a probe 3 provided to a target object 2 directly or through a delay material such as water. The probe 3 converts the pulse signal into an ultrasonic pulse a and applies the ultrasonic pulse a to the target object 2. The ultrasonic pulse a applied into the target object 2 is reflected by a bottom surface 2a of the target object 2 and received by the probe 3 again. The probe 3 converts the reflected wave into an electrical signal and transmits the electrical signal to the ultrasonic transmit-receive unit 1. The ultrasonic transmit-receive unit 1 amplifies the received electrical signal and transmits the electrical signal to the A/D converter 11 as an echo signal b.

The A/D converter 11 uses the frequency of the clock signal b as a sampling frequency $f_S$ and converts the echo signal b into an n-bit digital signal. An echo signal $b_1$ converted into the digital signal is applied to a data input terminal $D_1$ of the FIFO register 12.

On the other hand, the ultrasonic transmit-receive unit 1 transmits a trigger signal c to the delay circuit 13 in synchronism with a timing at which the pulse signal is transmitted to the probe 3. The delay circuit 13 is constituted by a kind of counter. When the trigger signal c is input to the delay circuit 13, the delay circuit 13 begins to measure a delay time $T_D$ which is preset using the clock signal d. When the measurement of the delay time $T_D$ is ended, a start signal e is transmitted to the write time counter 14.

Note that the delay time $T_D$ is set to delay a measurement start time of the echo signal b when water or any other delay material is inserted between the probe 3 and the target object 2. In the device of this embodiment, the distance between the probe 3 and the target object 2 is set to be 100 mm in water, and, in order to capture a reflected wave from the target object 2, the delay time $T_D$ is set to satisfy $$T_D = 2 \times 100 mm / 1,480 m/s = 135 \mu s$$

Note that the speed of an ultrasonic wave in water is set to be 1,480 m/s.

Figure 3:
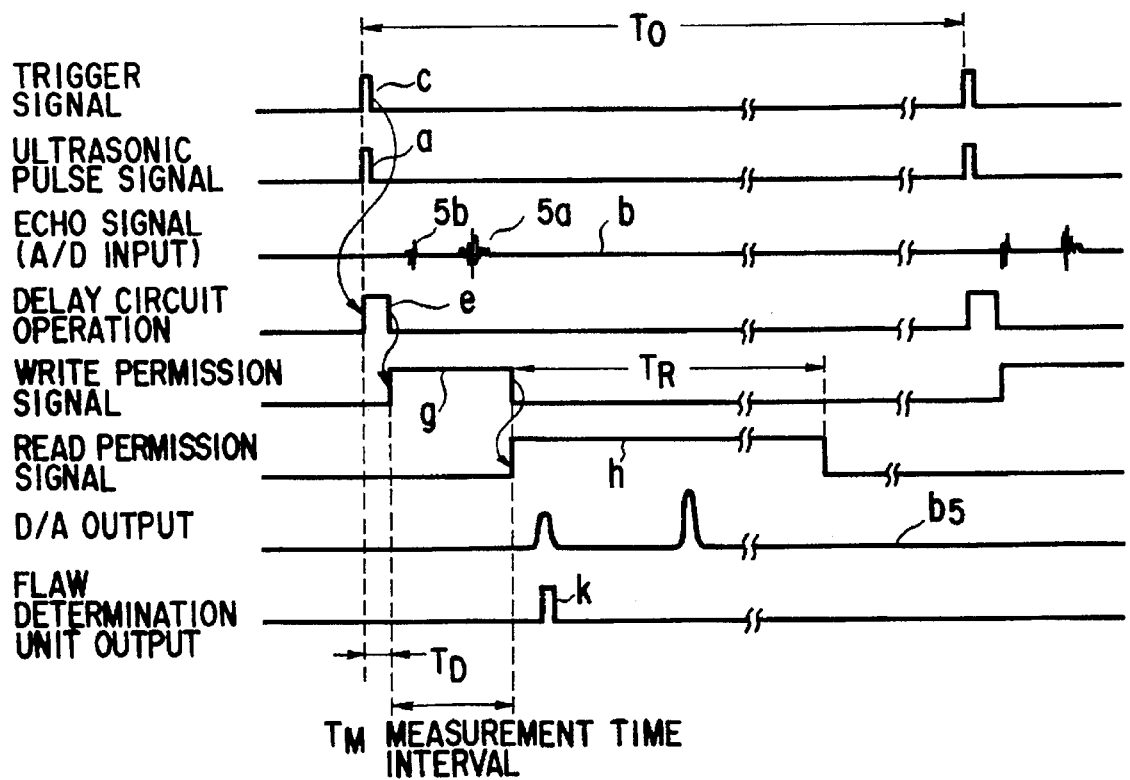
FIG. 3 is a timing chart showing the operation of the device of the embodiment in FIG. 1.

When the start signal e is input to the write time counter 14, as shown in FIG. 3, the write time counter 14 transmits a write permission signal g to the write control terminal of the FIFO register 12. When a predetermined measurement time interval $T_M$ is ended, the write time counter 14 releases the write permission signal g. Note that the write permission signal g is also transmitted to the next read counter 15.

The read time counter 15 transmits a read permission signal h to the read control terminal of the FIFO register 12 in synchronism with the fall timing of the write permission signal g. When a predetermined read time interval $T_R$ is ended, the read time counter 15 releases the read permission signal h. This read permission signal h is also transmitted to a synchronous adding/averaging filter 17. Note that, in this embodiment, the read time $T_R$ is set to be a value five times the measurement time interval $T_M$. The measurement time interval $T_M$ includes $N_M$ (=1,024) sampling data.

On the other hand, the frequency divider 16 divides the frequency $f_S$ (=25 MHz) of the input clock signal d into 1/5 (N=5) frequencies to form frequency-divided clock signals $d_1$ (frequency $f_R$=5 MHz), and the frequency divider 16 applies the frequency-divided clock signals $d_1$ to the FIFO register 12, a digital filter 18, and the synchronous adding/averaging filter 17.

The FIFO register 12 sequentially stores, at a write frequency $f_W$ equal to the frequency (sampling frequency) of the clock signal d, n-bit sampling data input to the data input terminal $D_1$ in a time interval (measurement time interval $T_M$) in which the write permission signal g is set at H level. In this embodiment, a total of 1,024 sampling data are written. Sampling data stored in a time interval (read time interval $T_R$) in which the read permission signal h is set at H level are sequentially output from a data output terminal $D_2$ at a read frequency $f_R$ equal to the frequency of the frequency-divided clock signal $d_1$. Digital echo signals $b_2$ sequentially read out at the read frequency $f_R$ are input to the next digital filter 18.

Figure 2:
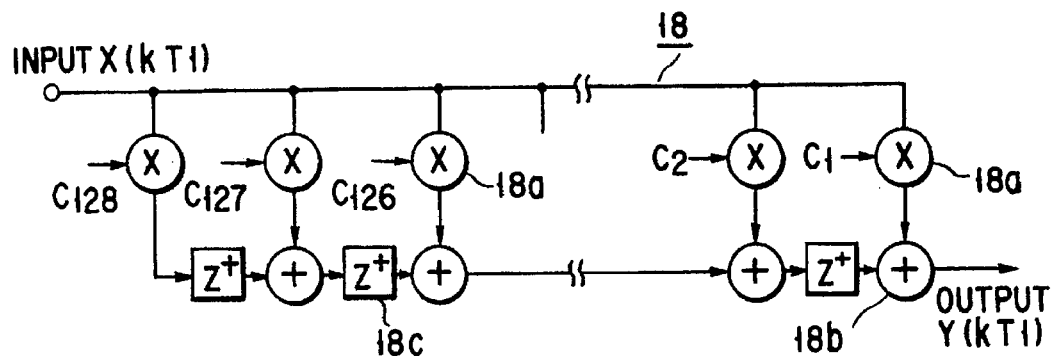
FIG. 2 is a view showing the schematic arrangement of a digital filter incorporated in the device of the embodiment in FIG. 1.

As can be seen in FIG. 2, the digital filter 18 is constituted by a 128th order FIR digital filter operated at the frequency ($f_R$=5 MHz) of the frequency-divided clock signal $d_1$. That is, this FIR digital filter is constituted by 128 multipliers 18a, 128 adders 18b, and 128 delay units 18c. Note that reference symbols $C_1$ to $C_{128}$ denote coefficients. Each delay unit 18c performs delay of 200 ns corresponding to a period $T_1$ of the frequency-divided clock signal $d_1$. This FIR digital filter calculates the sum of products represented by equation (2) with respect to a total of 1,024 input data $x(kT_1)$ which are sequentially input, thereby obtaining output data $y(kT1)$.

$$y(kT_1) = \sum_{i=1}^{128} Ci \cdot x(kT_1 - iT_1) \qquad (2)$$

$$k = -\infty \text{ to } \infty$$

Note that a frequency discrimination processing operation represented by equation (2) is performed within the period $T_1$(=200 ns), as a matter of course.

A digital echo signal $b_3$ to which the digital filter 18 performs the frequency discrimination processing operation represented by equation (2) is input to the next synchronous adding/averaging filter 17.

The synchronous adding/averaging filter 17 calculates the average of the 1,024 data constituting the echo signals $b_3$ represented by equation (2) and sequentially output from the digital filter 18 every repetitive period $T_0$. More specifically, the synchronous adding/averaging filter 17 calculates, in synchronous with rising of the read permission signal h from the read time counter 15, the added average of the data, which is output from the digital filter 18, of a previously predetermined number of times at the same timing position. The synchronous adding/averaging filter 17 transmits the added average to a next flaw determination unit 19 as a new averaged echo signal $b_4$.

In the flaw determination unit 19, a D/A converter 19a converts the input averaged echo signal $b_4$ into an analog echo signal $b_5$. The echo signal $b_5$ is compared with a predetermined threshold voltage $V_S$ by a comparator 19b. When there is an echo exceeding the threshold voltage $V_S$, a flaw signal k is transmitted to a next display unit 20. In addition, the analog echo signal $b_5$ is also transmitted to the display unit 20. The display unit 20 displays the echo signal $b_5$ and presence/absence information of a flaw.

The operation of the signal processing device of the ultrasonic inspection apparatus will be described using a timing chart shown in FIG. 3.

The trigger signal c is output in synchronism with transmission of the ultrasonic pulse a. The echo signal b is output from the ultrasonic transmit-receive unit 1. The echo signal b is converted into the digital echo signal $b_1$ by the A/D converter 11. When the delay time $T_D$ caused by a delay material such as water has passed after the trigger signal c is output, the write permission signal g rises, and 1,024 sampling data of the digital echo signal $b_1$ output from the A/D converter 11 are written in the FIFO register 12. A time, i.e., the measurement time interval $T_M$, required for writing the 1,024 (=NM) sampling data is a total of 40.96 µs because the sampling data are written at the same frequency as the sampling frequency $f_S$ (25 MHz) of the A/D converter 11 and a time required for writing one data is 40 ns.

When the write operation is ended, the read permission signal h rises, and the 1,024 sampling data stored in the FIFO register 12 are sequentially read out. Since the data are read out at the read frequency $f_R$ of 5 MHz, a time required to read out the data is 5 times the time required for writing the data. Therefore, the read time $T_R$ is set to be 40.49×5= 203 µs. For example, when data having an echo signal waveform shown in FIG. 4A is read out, as shown in FIG. 4B, a time axis is magnified 5 times.

The operation time of the digital filter 18 will be considered below. In the frequency divider 16, the frequency $f_R$ of the clock signal $d_1$ is 5 MHz which is ⅕ the previous sampling frequency $f_S$. For this reason, the read interval of the sampling data becomes 200 ns, and an operation time for the echo signal $b_2$ in one repetitive period $T_0$ of the ultrasonic pulse a is 1,024×200 ns=204.8 µs.

The operation time of the synchronous adding/averaging filter 17 will be considered below. This synchronous adding/averaging filter 17 starts an operation 128×200 ns=25.6 µs after a digital signal which is effective as an output signal begins to be output from the digital filter 18. The operation time becomes 204.8 µs because the output interval of data output from the digital filter 18 is 200 ns.

Note that a time required for determination can be almost neglected because the flaw determination unit 19 is constituted by an analog circuit.

In this manner, a digital pulse signal process for the echo signal b output in accordance with one ultrasonic pulse a can be satisfactorily performed within 0.5 ms which is the repetitive period $T_0$ of the ultrasonic pulse a required for an on-line inspection process. Therefore, since a high-performance computer having a very high operation processing speed need not be used, the cost of manufacturing an overall ultrasonic inspection apparatus is not considerably increased even when a digital signal process is employed.

In addition, a digital filter processing operation or a synchronous adding/averaging filter processing operation can be easily performed to the high-frequency echo signal b including a large amount of electrical noise and material noise. For this reason, when optimal filter conditions for the type of a material or measurement conditions are set, the noise component included in the echo signal can be effectively removed, and the flaw detection accuracy of the ultrasonic inspection apparatus can be considerably improved.

FIG. 5 is a block diagram showing the schematic arrangement of a signal processing device of an ultrasonic inspection apparatus according to another embodiment of the present invention. The same reference numerals as in the embodiment of FIG. 1 denote the same parts in FIG. 5. Therefore, the detailed description of the overlapping parts will be omitted.

In this embodiment, a clock signal $d_1$ having a frequency ⅕-divided by a frequency divider 16 is input to the clock terminal of a read time counter 15a. In the read time counter 15a, a read time $T_R$ shown in FIG. 3 is measured. For this reason, an effect which is almost the same as that of the embodiment in FIG. 1 can be obtained.

Figure 6:
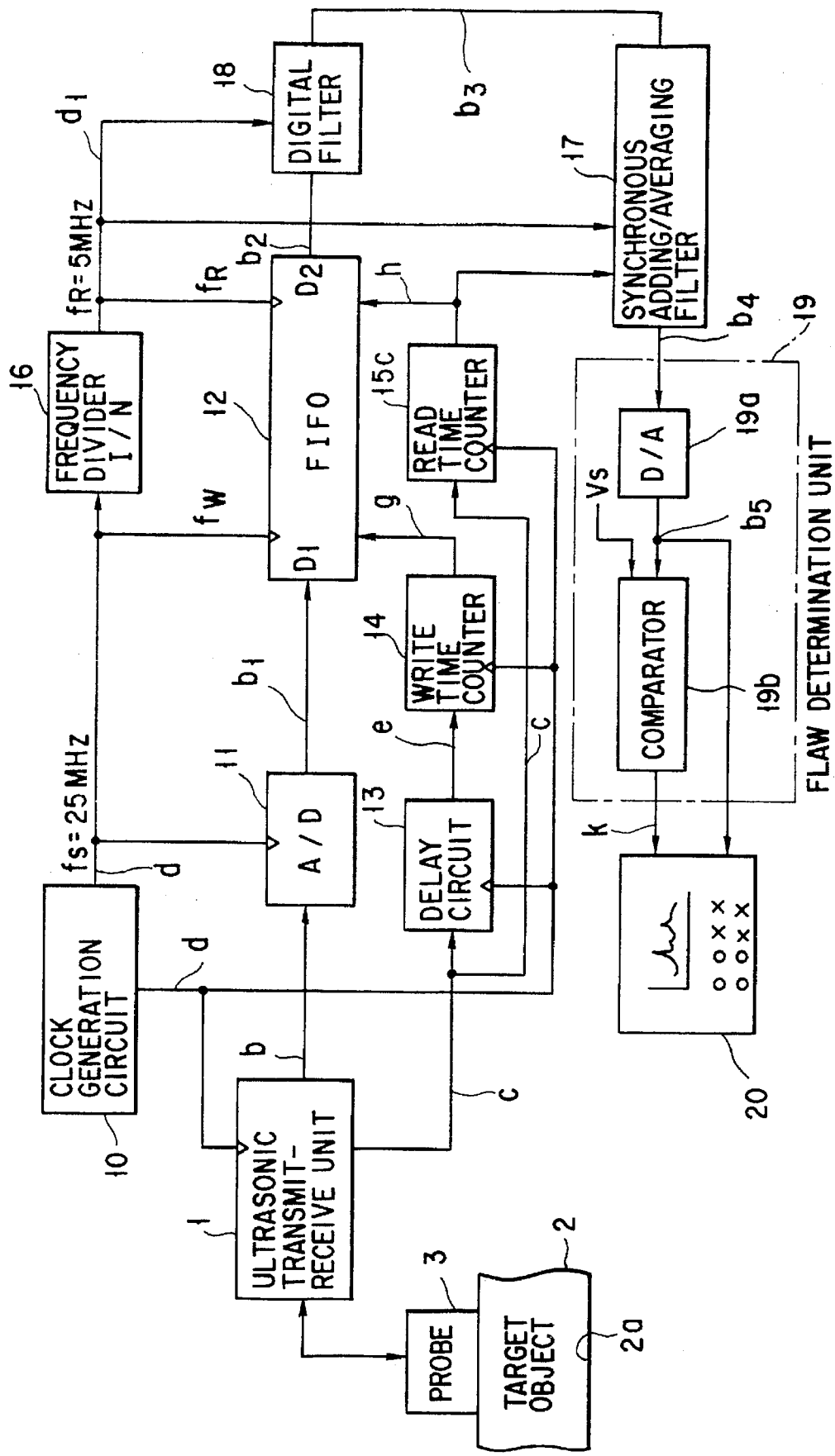
FIG. 6 is a block diagram showing the schematic arrangement of an ultrasonic inspection apparatus in which a signal processing device of still another embodiment is incorporated.

FIG. 6 is a block diagram showing the schematic arrangement of a signal processing device of an ultrasonic inspection apparatus according to still another embodiment of the present invention. The same reference numerals as in the embodiment of FIG. 1 denote the same parts in FIG. 6. Therefore, a detailed description of the overlapping parts will be omitted.

In this embodiment, a write permission signal g output from a write time counter 14 is transmitted to only a FIFO register 12 and is not transmitted to a read time counter 15c. A trigger signal c output from an ultrasonic transmit-receive unit 1 is input to the read time counter 15c. When the trigger signal c is input to this read time counter 15c, the read time counter 15c begins to measure a waiting time ($T_R+T_M$) obtained by adding a delay time $T_R$ and a measurement time $T_M$, which are shown in FIG. 3, to each other. When the measurement of the waiting time ($T_R+T_M$) is ended, a read permission signal h is set at H level. When the measurement of the read time $T_R$ is ended, this H-level read permission signal h is reset to be L level.

Therefore, since the read time counter 15c measures the read time $T_R$ shown in FIG. 3, the effect which is almost the same as that of the embodiment in FIG. 1 can be obtained.

Figure 7:
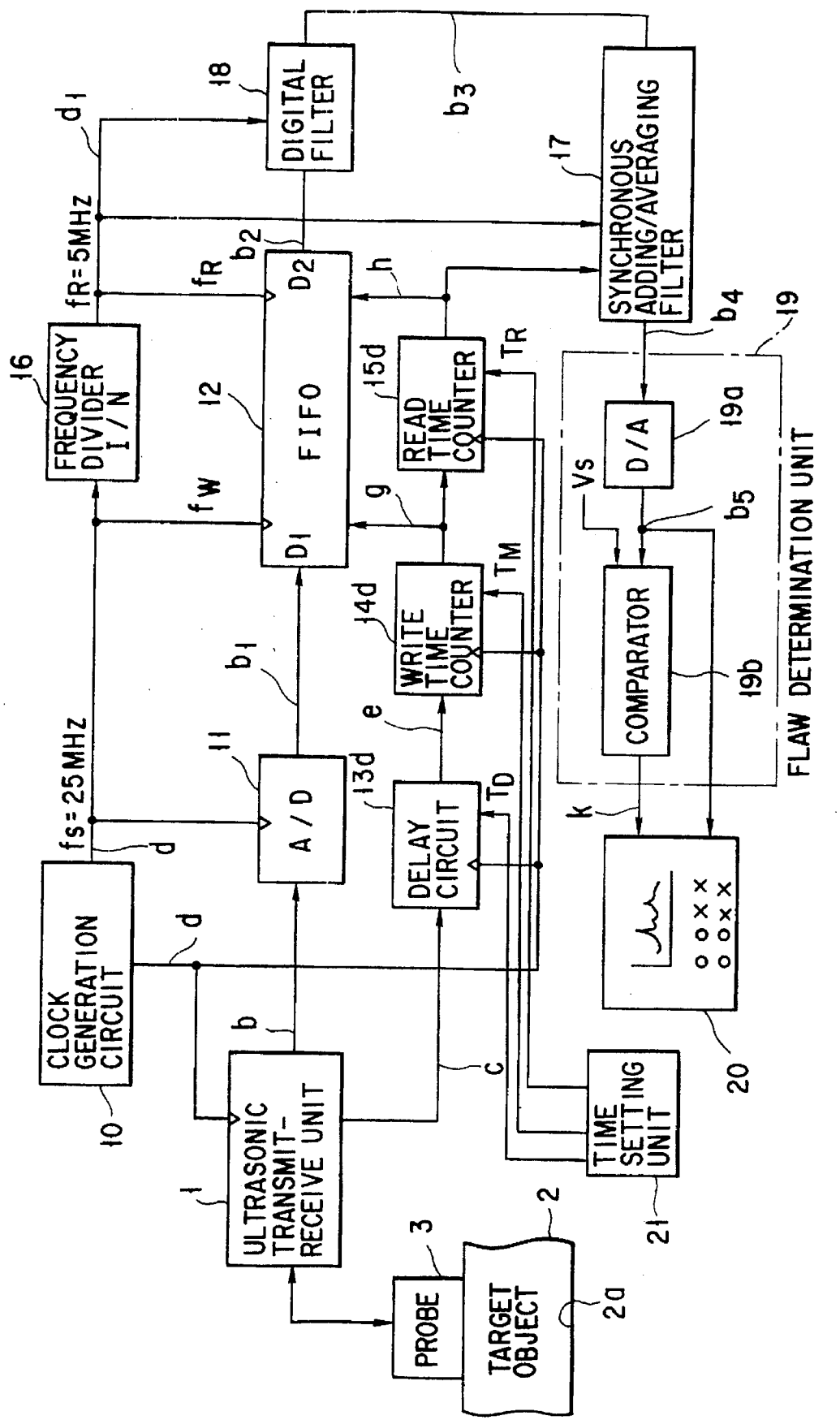
FIG. 7 is a block diagram showing the schematic arrangement of an ultrasonic inspection apparatus in which a signal processing device of still another embodiment is incorporated.

FIG. 7 is a block diagram showing the schematic arrangement of a signal processing device of an ultrasonic inspection apparatus according to still another embodiment of the present invention. The same reference numerals as in the embodiment of FIG. 1 denote the same parts in FIG. 7. Therefore, a detailed description of the overlapping parts will be omitted.

In this embodiment, a delay time $T_D$ measured by a delay circuit 13d, a measurement time interval $T_M$ measured by a write time counter 14d, a read time $T_R$ measured by a read time counter 15d can be arbitrarily set and changed by an external time setting unit 21.

There are various types of target objects 2 to be inspected by the ultrasonic inspection apparatus. Therefore, depending on the shape of the target object 2, an area to be inspected may have to be designated as a portion shallow from the surface, a portion deep from the surface, or the like. In addition, the thickness of the target object 2 considerably changes. As described above, when the area to be inspected is changed or enlarged/reduced, the position of the measurement time interval $T_M$ in the echo signal a must be shifted, or the measurement time interval $T_M$ must be prolonged or shortened. In this case, the time setting unit 21 sets the delay time $T_D$, the measurement time interval $T_M$, and the read time $T_R$ to be optimal values. Therefore, the scope of application of the ultrasonic defect detecting apparatus in which the signal processing device is incorporated can be considerably widened.

Figure 8:
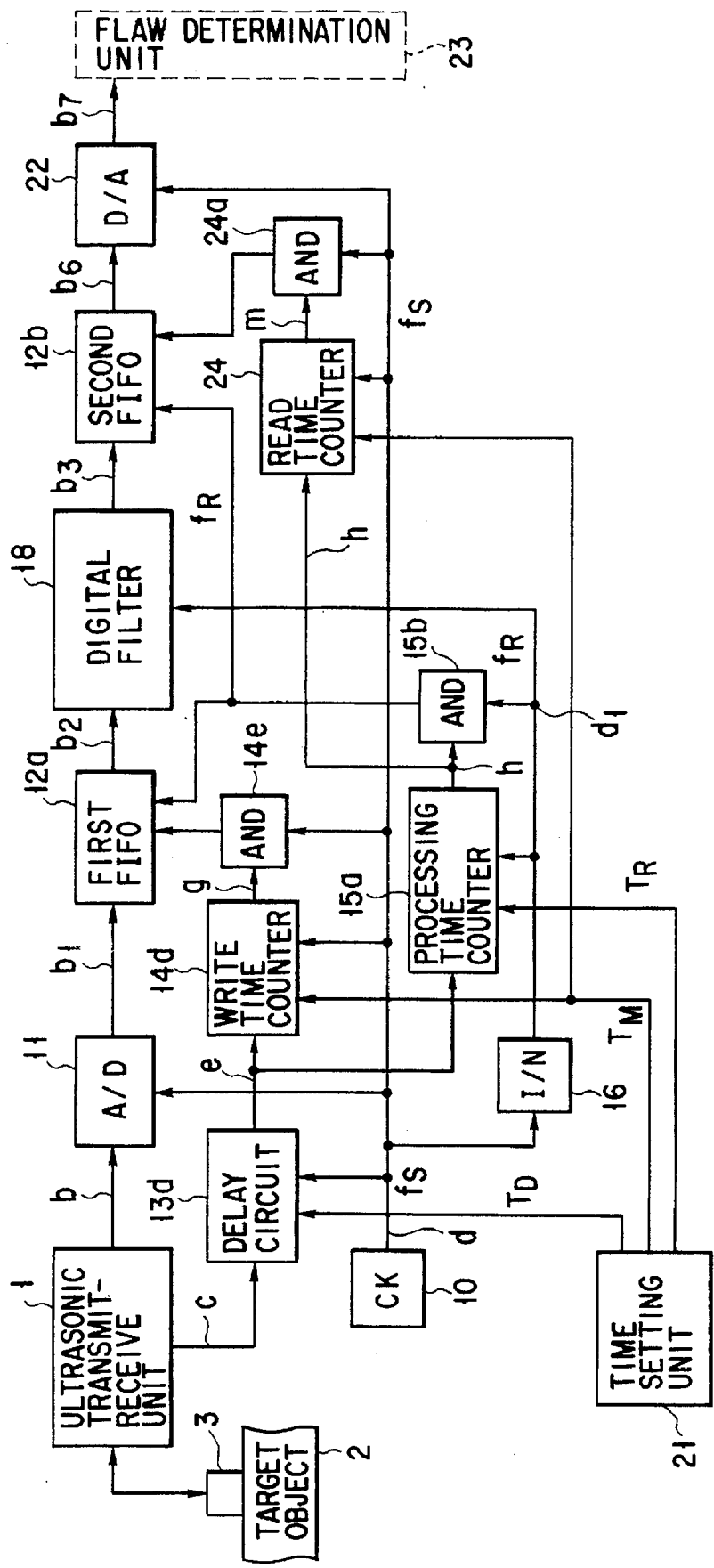
FIG. 8 is a block diagram showing the schematic arrangement of an ultrasonic inspection apparatus in which a signal processing device of still another embodiment is incorporated.

FIG. 8 is a block diagram showing the schematic arrangement of a signal processing device of an ultrasonic inspection apparatus according to still another embodiment of the present invention. The same reference numerals as in the embodiment of FIG. 7 denote the same parts in FIG. 8. A detailed description of the overlapping parts will be omitted.

In this embodiment, an A/D converter 11, a first FIFO register 12a, a digital filter 18, a second FIFO register 12b, a D/A converter 22, and an external flaw determination unit 23 are arranged along the signal path of an echo signal b output from an ultrasonic transmit-receive unit 1.

A clock signal d output from a clock signal generation circuit 10 and having a sampling frequency $f_S$ is applied to the write clock terminal of the first FIFO register 12a through an AND gate 14e and applied to the read clock terminal of the second FIFO register 12b through an AND gate 24a. In addition, the clock signal d is applied to the clock terminal of the D/A converter 22.

A clock signal $d_1$ having a frequency $f_R$ (=$f_S/5$) and output from a frequency divider 16 is applied to the read clock terminal of the first FIFO register 12a and the write clock terminal of the second FIFO register 12b through an AND gate 15b and applied to the clock terminal of the digital filter 18.

A start signal e output from a delay circuit 13d is applied to a write time counter 14d and a processing time counter 15a. The write time counter 14d, as shown in a timing chart in FIG. 9, applies an H-level write permission signal g to the AND gate 14e for only a measurement time interval (A/D conversion time) $T_M$. As a result, the first FIFO register 12a sequentially receives and stores, at a write frequency equal to the sampling frequency $f_S$, the sampling data of a digital echo signal $b_1$ output from the A/D converter 11 for only the measurement time interval (A/D conversion time) $T_M$.

In addition, the processing time counter 15a applies an H-level read permission signal h to art AND gate 15b for only a read time (signal processing time) $T_R$ set by a time setting unit 21. As a result, the first FIFO register 12a sequentially reads out, at a read frequency $f_R$ which is ⅕ the sampling frequency $f_S$, data stored for only the read time (signal processing time) $T_R$ and transmits the data to the digital filter 18 as a digital echo signal $b_2$.

The digital filter 18 performs the above-described frequency discrimination process in real time to echo signals $b_2$ which are sequentially input to the digital filter 18 at a speed corresponding to the read frequency $f_R$ to transmit an echo signal $b_3$ whose noise component is removed to the second FIFO register 12b.

A read permission signal h, for the first FIFO register 12a, output from the processing time counter 15a is applied to not only the AND gate 15b but also a read time counter 24. The read time counter 24 applies, to the AND gate 24a, a read permission signal m which is set at H level for only the read time (measurement time) $T_M$ set by the time setting unit 21 from rise time at which the read permission signal h for the first FIFO register 12a goes from H level to L level.

Figure 9:
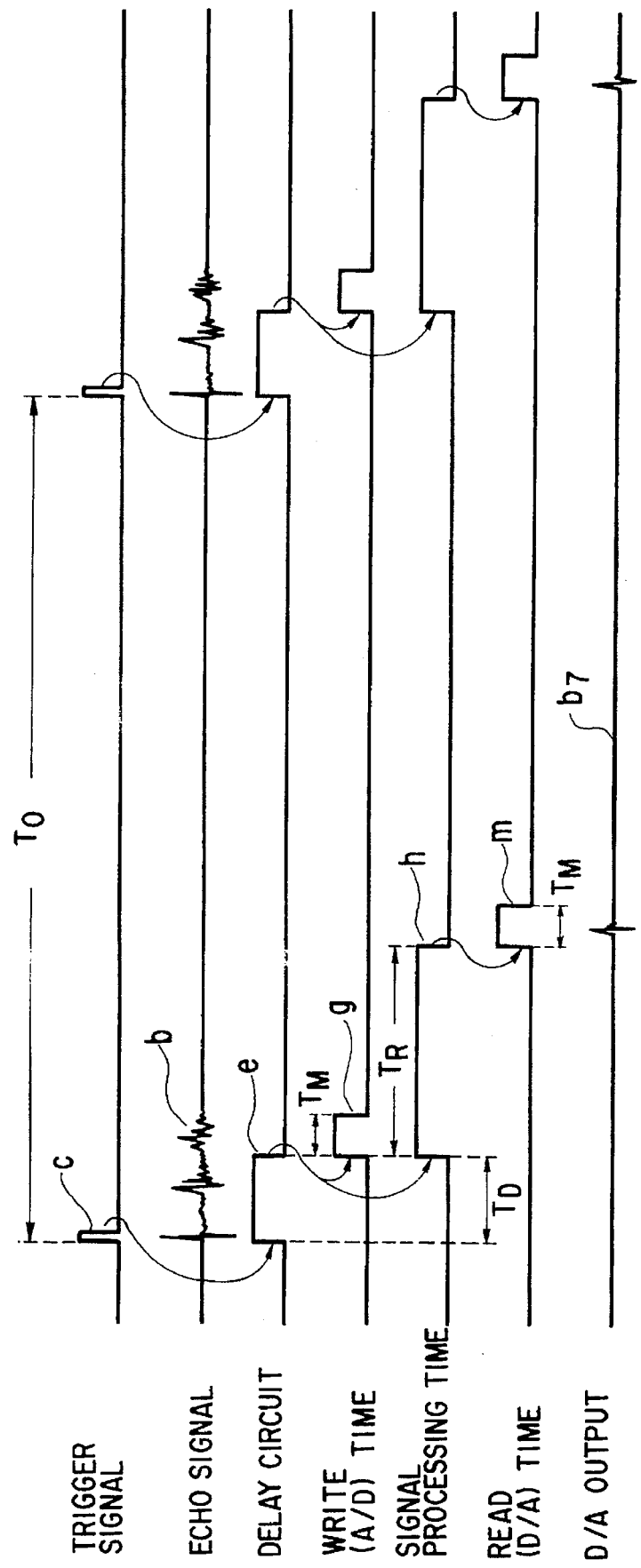
FIG. 9 is a timing chart showing the operation of the device of the embodiment in FIG. 8.

Therefore, the second FIFO register 12b, as shown in FIG. 9, in synchronism with the read start time of the echo signal $b_2$ of the first FIFO register 12a, sequentially receives and stores the data of the echo signal $b_3$ output from the digital filter 18 at a write frequency equal to the read frequency $f_R$ of the first FIFO register 12a. When the signal processing time (read time) $T_R$ is ended, and all the data of the echo signal $b_3$ are stored, the second FIFO register 12b reads out the stored data at a 5-time read frequency which is equal to the original sampling frequency $f_S$ to apply the data to the next D/A converter 22 as an echo signal $b_6$.

The D/A converter 22 receives the data of the echo signal $b_6$ at the sampling frequency $f_S$ and converts the data into an analog echo signal $b_7$ to transmits the echo signal $b_7$ to the external flaw determination unit 23.

FIG. 9 is a timing chart showing the operation of the device of the embodiment shown in FIG. 8. As shown in FIG. 9, a delay circuit 13d measures a delay time $T_D$ in synchronism with a trigger signal c. Therefore, measurement of the write time (measurement time interval) $T_M$ and the signal processing time (read time) $T_R$ is started. When the signal processing time (read time) $T_R$ is ended, the read time $T_M$ for the second FIFO register 12b is started.

In the signal processing device of the ultrasonic inspection apparatus arranged as described above, in only a time interval in which a frequency discrimination process is performed to an input echo signal in the digital filter 18, the time axis of the echo signal is magnified 5 times from 25 MHz to 5 MHz. When the frequency discrimination process in the digital filter 18 is ended, the time axis is returned to the original axis to convert the echo signal into the analog echo signal $b_7$.

A flaw determination process for the analog echo signal $b_7$ can be satisfactorily performed even if a defect event in the echo signal occurs at a high frequency of about 25 MHz. Therefore, when this analog echo signal $b_7$ is applied to a general ultrasonic inspection unit, inspection can be easily performed to a target object 2.

In this case, since the noise component of the echo signal $b_7$ is considerably suppressed by the digital filter 18, the general ultrasonic inspection unit can detect a flaw at high accuracy.

Figure 10:
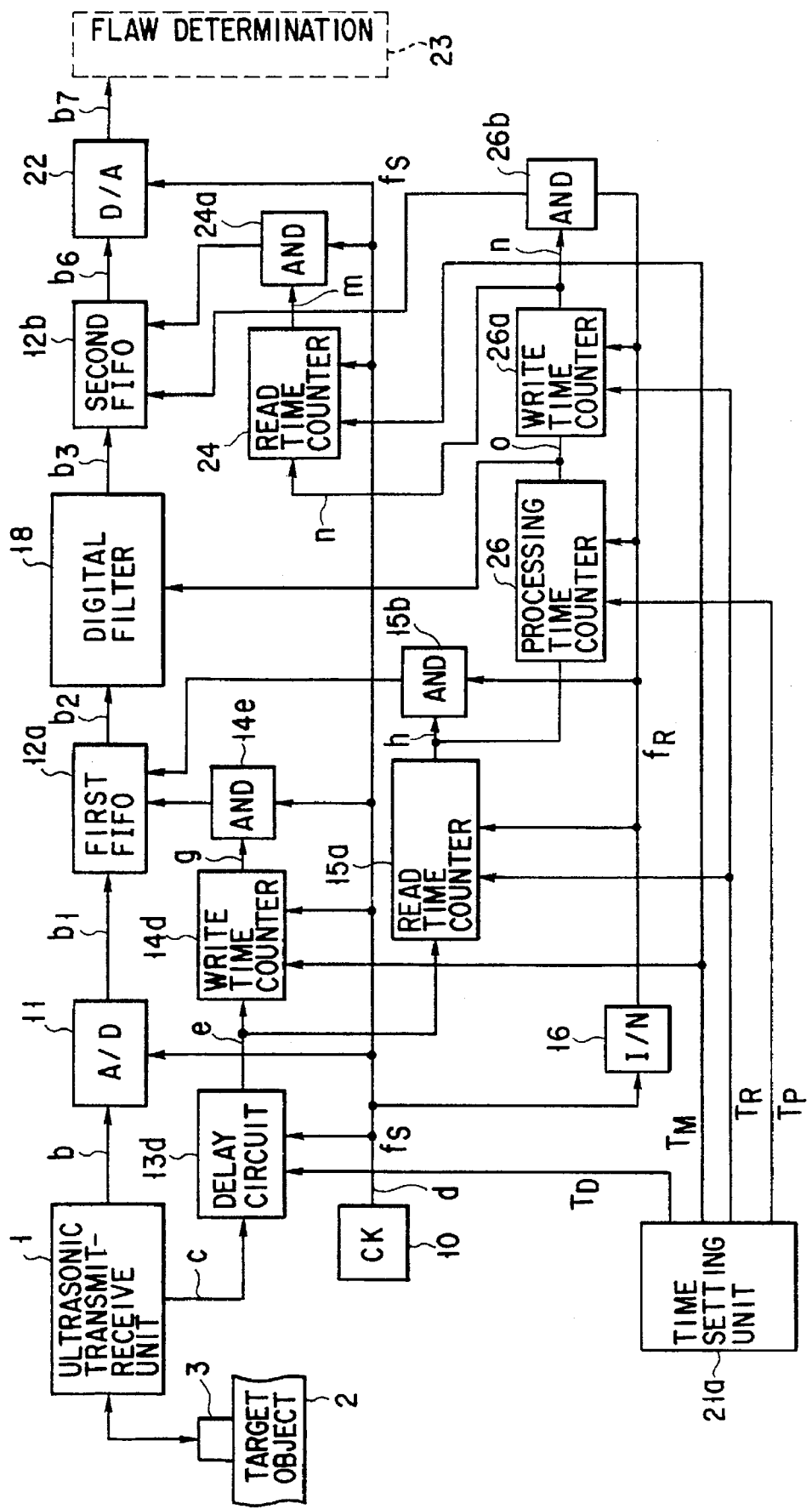
FIG. 10 is a block diagram showing the schematic arrangement of an ultrasonic inspection apparatus in which a signal processing device of still another embodiment is incorporated.

FIG. 10 is a block diagram showing the schematic arrangement of a signal processing device of an ultrasonic inspection apparatus according to still another embodiment of the present invention. The same reference numerals as in the embodiment of FIG. 8 denote the same parts in FIG. 10. Therefore, the detailed description of the overlapping parts will be omitted.

In this embodiment, as a digital filter 18a, a filter is used in which, after all the data of an echo signal $b_2$ output from a first FIFO register 12a are temporarily stored in the multiplier 18a, a frequency discrimination process is performed using all the data, and, upon completion of this process, the process result is output as a digital echo signal $b_6$.

Therefore, a time setting unit 21a sets, in addition to a delay time $T_D$, a write time (measurement time interval) $T_M$, and a read time $T_R$, a data processing time $T_P$ required for the frequency discrimination process in the digital filter 18.

A read permission signal h of a read time counter 15a for the first FIFO register 12a is applied to an AND gate 15b and applied to a data processing time counter 26. The data processing time counter 26, as shown in a timing chart of FIG. 11, in synchronism with rising of the read permission signal h, begins to measure the data processing time $T_P$ set by the time setting unit 21a and outputs an H-level data processing time signal o.

When the data processing time $T_P$ is ended, the data processing time signal o falls to L level, and a next write time counter 26a applies, to an AND gate 26b, a write permission signal n which is kept set at H level for only a time corresponding to the read time $T_R$ and applies the write permission signal n to a read time counter 24 of a second FIFO register 12b.

Figure 11:
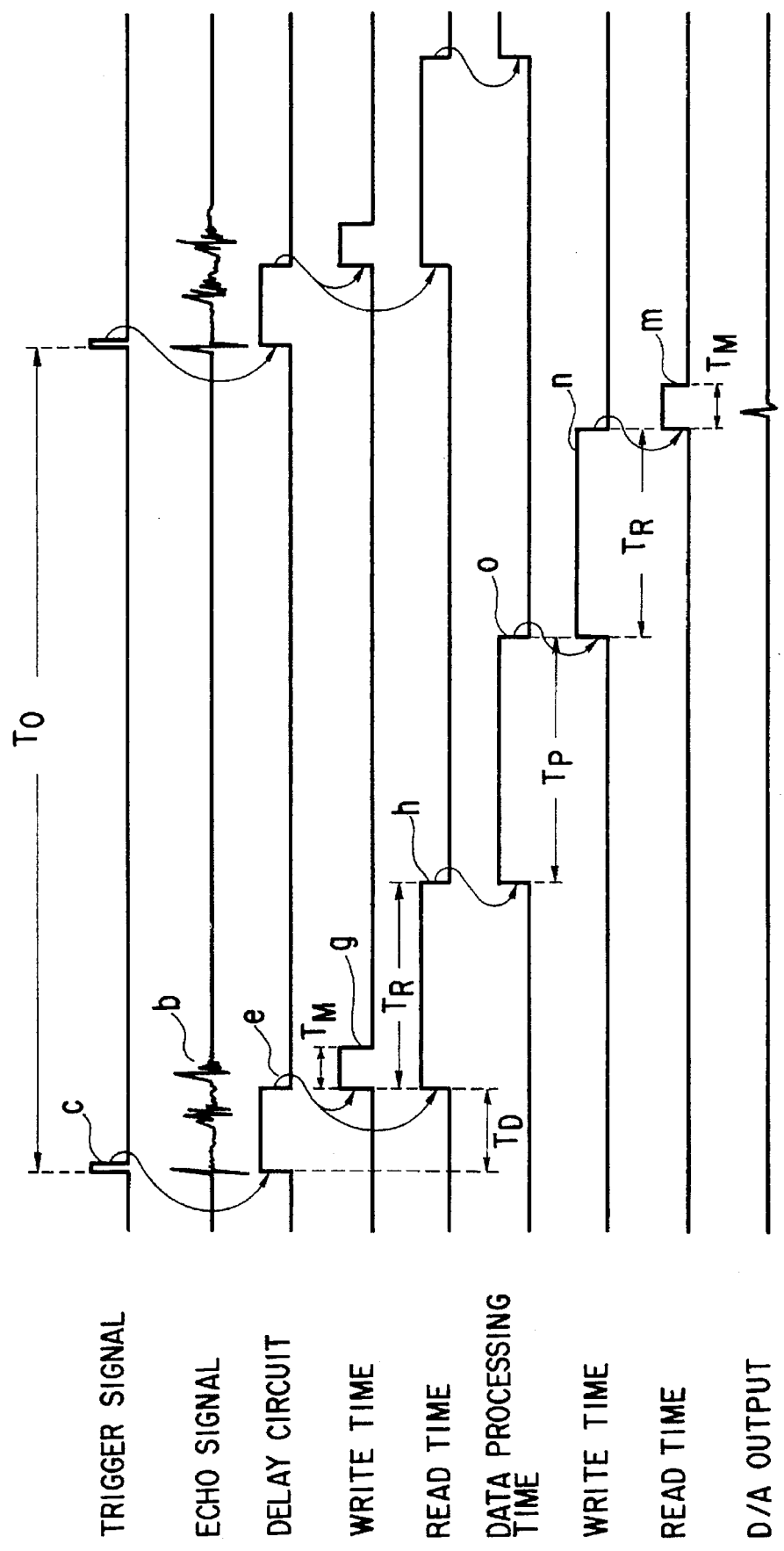
FIG. 11 is a timing chart showing the operation of the device of the embodiment in FIG. 10.

Therefore, as shown in the timing chart of FIG. 11, when the data processing time $T_P$ in the digital filter 18 is ended, the second FIFO register 12b writes the data of an echo signal $b_3$ output from the digital filter 18 at a frequency $f_R$ which is ⅕ a sampling frequency $f_S$. When the write process of all the data is ended, the data are sequentially read out at the original high sampling frequency $f_S$ and applied to a next D/A converter 22 as the echo signal $b_6$.

In the signal processing device of the ultrasonic inspection apparatus arranged as described above, since the echo signal $b_3$ to which the digital filter 18 performs a frequency discrimination process can be returned to the echo signal $b_6$ having an original time axis by using the second FIFO register 12b, an effect which is almost the same as that of the embodiment shown in FIG. 8 can be obtained.

In addition, in this embodiment, when the data processing time $T_P$ of the time setting unit 21a is changed, the contents of a frequency discrimination process in the digital filter 18a can be arbitrarily changed.

Figure 12:
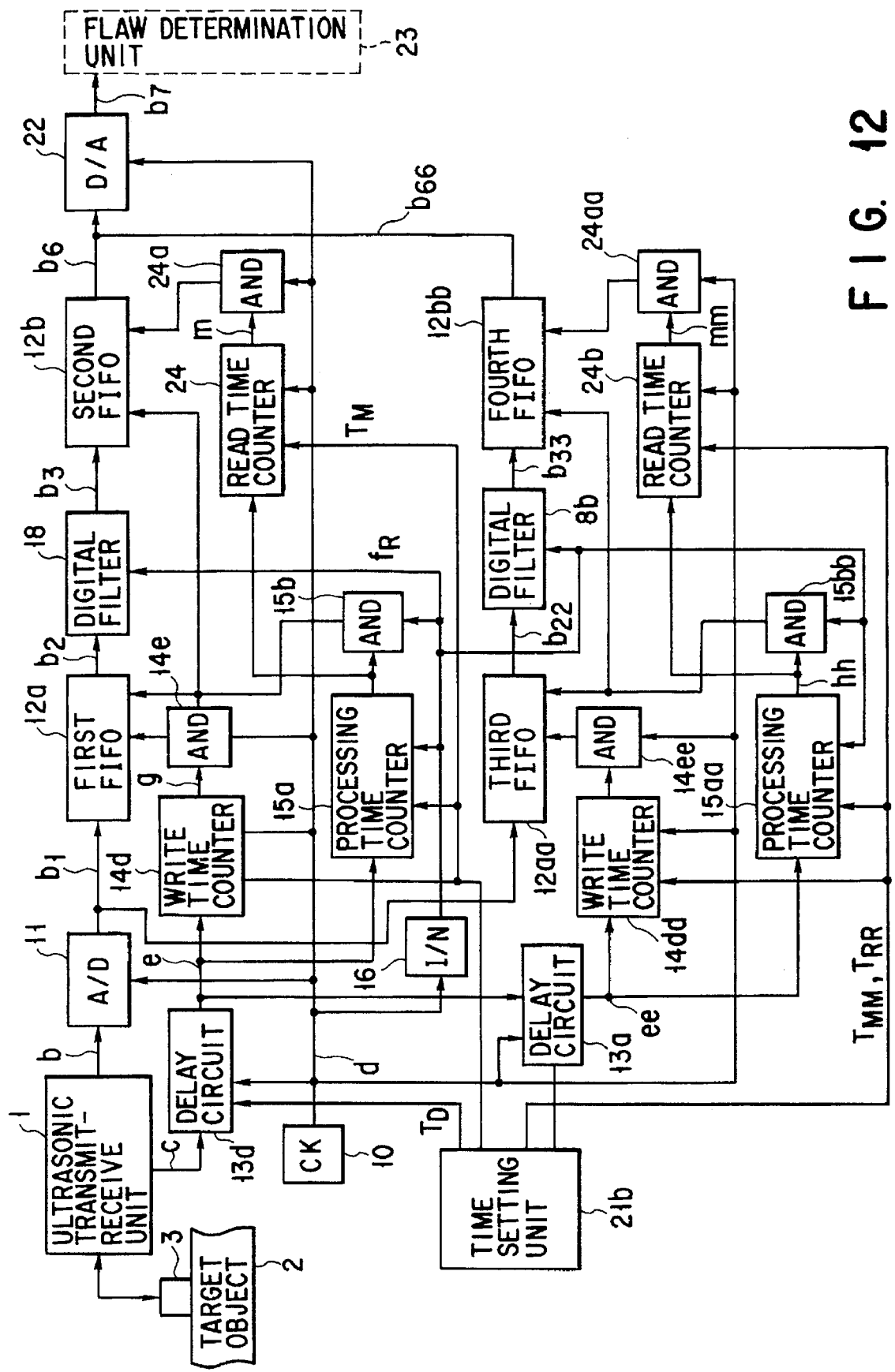
FIG. 12 is a block diagram showing the schematic arrangement of an ultrasonic inspection apparatus in which a signal processing device of still another embodiment is incorporated.

FIG. 12 is a block diagram showing the schematic arrangement of a signal processing device of an ultrasonic inspection apparatus according to still another embodiment of the present invention. The same reference numerals as in the embodiment of FIG. 8 denote the same parts in FIG. 12. Therefore, a detailed description of the overlapping parts will be omitted.

In this embodiment, another signal storage processing circuit constituted by a third FIFO register 12aa, a second digital filter 8b, and a fourth FIFO register 12bb is parallelly connected to a signal storage processing circuit constituted by a first FIFO register 12a, a first digital filter 18, and a second FIFO register 12b of an A/D converter 11, the first FIFO register 12a, the first digital filter 18, the second FIFO register 12b, and a D/A converter 22 which are inserted in the signal path of an echo signal output from an ultrasonic transmit-receive unit 1 shown in FIG. 8.

In a time setting unit 21b, with respect to a delay time $T_D$, a write time (measurement time) $T_M$, a read (processing time) $T_R$ for the first and second FIFO registers 12a and 12b of the upper signal storage processing circuit, a delay time $T_{DD}$, a write time (measurement time) $T_{MM}$, and read (processing time) $T_{RR}$ for the first and second FIFO registers 12aa and 12bb of the lower signal storage processing circuit can be respectively set.

Figure 13:
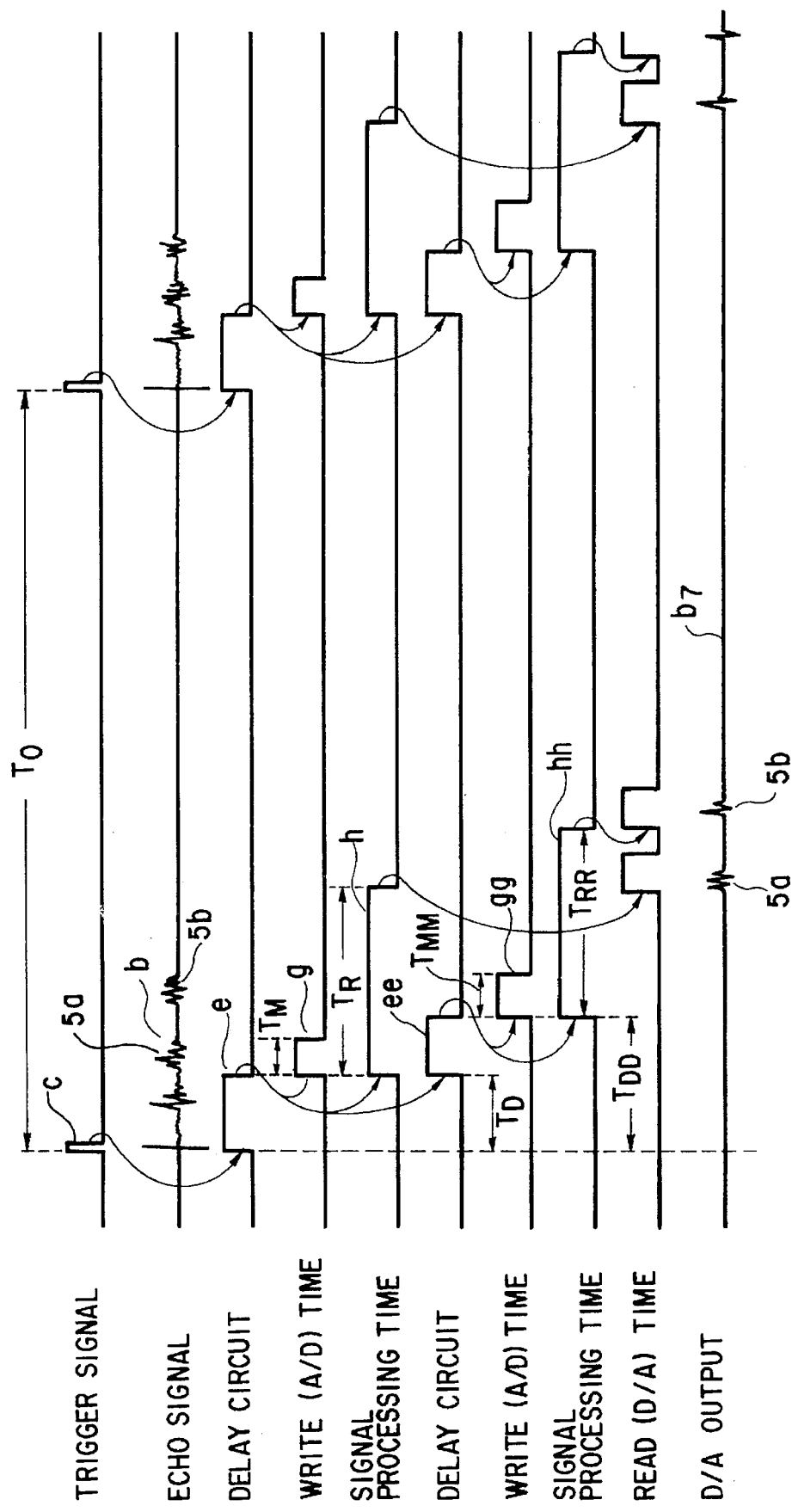
FIG. 13 is a timing chart showing the operation of the device of the embodiment in FIG. 12.

Therefore, as shown in a timing chart of FIG. 13, when the delay time $T_{DD}$ of the lower signal storage processing circuit is set to be equal to or longer than a time $(T_D+T_M)$ obtained by adding the write time (measurement time) $T_M$ to the delay time $T_D$ of the upper signal storage processing circuit, a plurality of flaw echoes 5a and 5b at different time positions on an echo signal b can be respectively extracted, thereby performing a frequency discrimination process using the digital filters 18 and 8b. Echo signals $b_6$ and $b_{66}$ subjected to a digital signal process are synthesized with each other, and one original analog echo signal $b_7$ can be obtained by the D/A converter 22.

With the above arrangement, not only an effect which is almost the same as that of the embodiment in FIG. 8 can be obtained, but also the plurality of flaw echoes 5a and 5b can be analyzed by the single A/D converter 11 and the single D/A converter 22.

In addition, the measurement times (write times) $T_M$ and $T_{MM}$ for the flaw echoes 5a and 5b on the echo signal b can be set to be optimal time widths in accordance with the scales and types of flaws.

FIG. 14 is a block diagram showing the schematic arrangement of a signal processing device of an ultrasonic inspection apparatus according to still another embodiment of the present invention. The same reference numerals as in the embodiment of FIG. 8 denote the same parts in FIG. 14. Therefore, a detailed description of the overlapping parts will be omitted.

In this embodiment, the digital filter 18 in the device of the embodiment shown in FIG. 8 is replaced with a synchronous adding/averaging circuit 27. This synchronous adding/averaging circuit 27 has a function of averaging, over a plurality of periods (Na times), a digital echo signal $b_2$ output from a first FIFO register 12a each time an output period $T_0$ of an ultrasonic pulse a has passed. A digital echo signal $b_8$ obtained by averaging Na echo signals $b_2$ is input to a next second FIFO register 12b.

The synchronous adding averaging circuit 27 performs an adding/averaging process of the echo signal $b_2$ using a frequency-divided clock signal $d_1$ output from a frequency divider 16 and having a frequency $f_R$.

Figure 15:
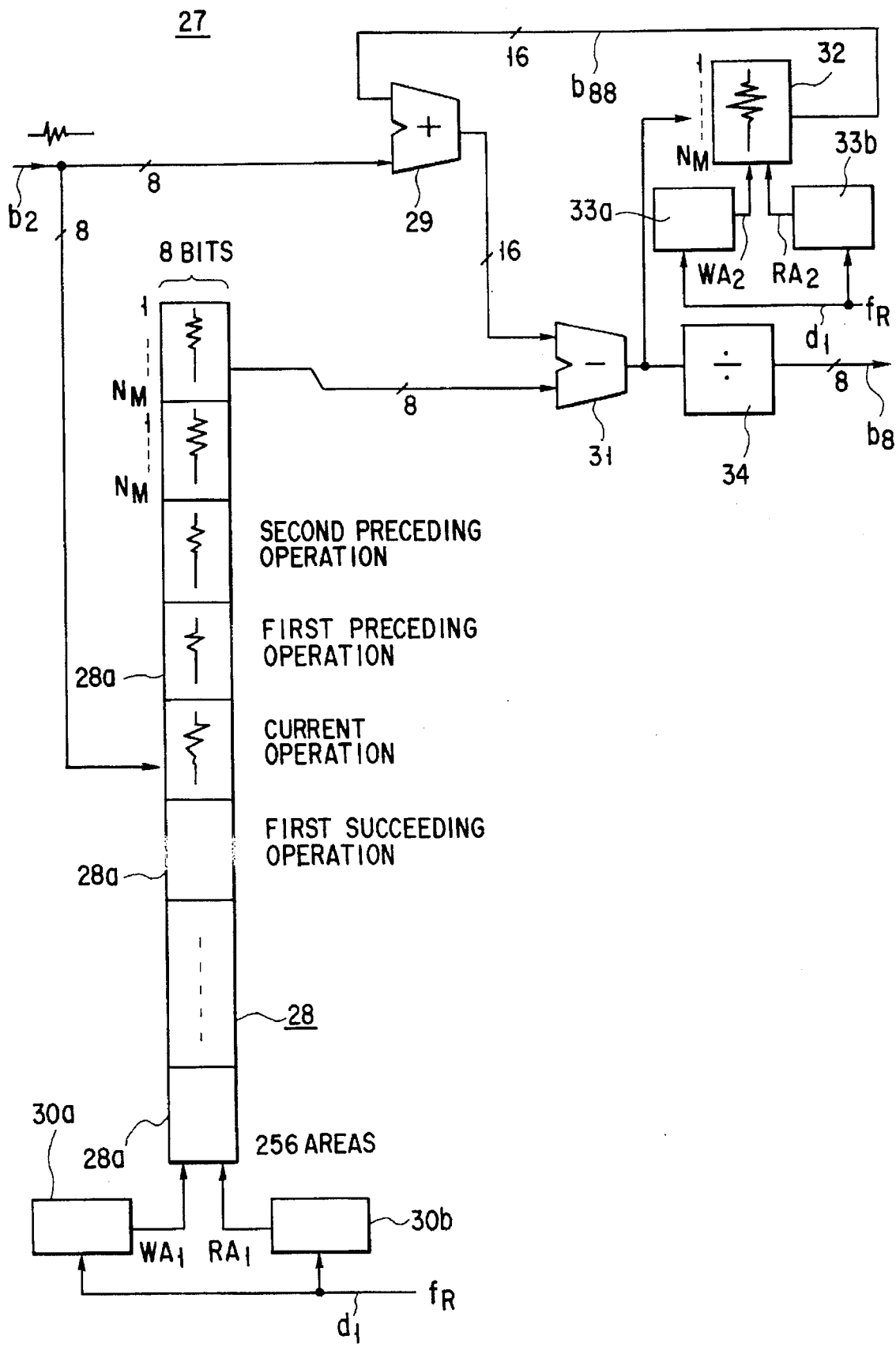
FIG. 15 is a block diagram showing the schematic arrangement of a synchronous adding/averaging circuit in the device of the embodiment in FIG. 14.

FIG. 15 is a block diagram showing the schematic arrangement of the synchronous adding/averaging circuit 27. $N_M$ (=1,024) 8-bit data constituting the echo signal $b_2$ sequentially read out from the first FIFO register 12a at a read frequency $f_R$ equal to the frequency $f_R$ of the frequency-divided clock signal $d_1$ are written in a first signal memory 28 and input to an adder 29 for performing a digital adding process.

In the first signal memory 28, as shown in FIG. 15, 256 areas 28a for storing the echo signals $b_2$ are formed. For this reason, each area 28a has $N_M$ (=1,024) addresses, and 8-bit data can be stored at each address. A write address $WA_1$ of the data constituting the echo signals $b_2$ for the first signal memory 28 is designated by a first write address counter 30a. In addition, a read address $RA_1$ used when the echo signal $b_2$ stored in the first signal memory 28 are to be read out is designated by a first read address counter 30b. The counters 30a and 30b are driven by the frequency-divided clock signal d1.

In addition, the read address $RA_1$ of the first read address counter 30b is initially set to have a value delayed (smaller) with respect to the write address $WA_1$ of the first write address counter 30a by an average number Na of times of the areas 28a.

$$RA_1 = WA_1 - N_M \cdot N^a$$

$$WA_1 - 1024 \cdot N^a \quad (3)$$

More specifically, the data of each input echo signal $b_2$ are sequentially stored at addresses designated by the write address $WA_1$ increased in synchronous with the frequency-divided clock signal $d_1$. At the same time, data at a waveform position identical to that of the echo signals $b_2$ stored in the first signal memory 28 in an Nath preceding operation is read out in synchronism with this write operation.

Note that, when the write address $WA_1$ and the read address $RA_1$ reach the final address of the first signal memory 28, the write address $WA_1$ and the read address $RA_1$ return to the start address.

The data of the echo signal $b_2$ stored in the Nath preceding operation and read from the first signal memory 28 is input to a subtracter 31 for performing a next digital subtracting process.

In addition, a second signal memory 32 has $N_M$ (=1,024) addresses, constituting one added echo signal b, i.e., an added echo signal $b_{88}$, for storing the added echo signal $b_{88}$, and 16-bit data can be stored at each address. The data of the added echo signal output from the subtracter 31 are sequentially written in the second signal memory 32. The added echo signal $b_{88}$ read out from the second signal memory 32 is input to the adder 29.

A write address $WA_2$ of each data of the added echo signal from the subtracter 31 is designated by a second write address counter 33a. In addition, a read address $RA_2$ of each data of the added echo signal $b_{88}$ transmitted to the adder 29 is designated by a second read address counter 33b. The counters 30a and 30b are driven by the frequency-divided clock $d_1$. In synchronism with the frequency-divided clock signal $d_1$, the four address counters 30a, 30b, 33a, and 33b are initially set such that identical positions on the waveform signals of an echo signal, i.e., identical addresses of the 1 to 1,024 addresses in each area 28a and the second signal memory 32 are designated.

The adder 29 adds 16-bit data constituting the added echo signal $b_{88}$ read out from the second signal memory 32 to 8-bit data constituting the input echo signal $b_2$ and transmits, to the subtracter 31, added echo signals each constituted by 16-bit data.

The subtracter 31 subtracts each 8-bit data of the echo signal read out from the first signal memory 28 from each 16-bit data of the added echo signal input from the adder 29. The added echo signal constituted by the subtracted 16-bit data is transmitted to the second signal memory 32 and transmitted to a divider 34.

The divider 34 is constituted by, e.g., a bit shifter. The divider 34 divides the added echo signal by an average number Na of times and transmits the calculation result to the second FIFO register 12b in FIG. 14 as an averaged echo signal $d_8$.

The operation of the synchronous adding/averaging circuit 27 arranged as described above will be described below.

First, in an initial state in which any echo signal $b_2$ is not input, any data of the echo signal is not stored in each area 28a of the first signal memory 28 and the second signal memory 32.

When the first echo signal $b_2$ is input from the first FIFO register 12a, the echo signal $b_2$ is stored in the start area 28a of the first signal memory 28. At the same time, the echo signal $b_2$ is stored in the second signal memory 32. Since any signal is not stored at each address of the areas 28a designated by the read address $RA_1$ of the second signal memory 32 and the first signal memory 28 at the beginning, the input echo signal $b_2$ is stored in the second signal memory 32 without being processed by the adder 29 and the subtracter 31.

When the second echo signal $b_2$ is input, the adder 29 adds a current echo signal to a first preceding (first) echo signal to form an added echo signal. However, when an average number Na of times >2 is satisfied, any signal is not stored at each address of the area 28a designated by the read address $RA_1$ of the first signal memory 28. For this reason, the added echo signal is stored in the second signal memory 32 without being processed by the subtracter 31.

In this manner, until echo signals $b_2$ having an average number Na of times are input, echo signals are sequentially added to the second signal memory 32. When the echo signals $b_2$ having the average number Na of times or more are input, an echo signal which is input ahead of a newly input echo signal $b_2$ by the number Na is read out and transmitted to the subtracter 31.

More specifically, when the new echo signal $b_2$ is input, the new echo signal $b_2$ is added to the added echo signal $b_{88}$ stored in the second signal memory 32, and an echo signal input in the Nath preceding operation is subtracted from the added echo signal $b_{88}$. Therefore, the second signal memory 32 always stores the added echo signal $b_{88}$ to which a latest number Na of echo signals are added.

Therefore, the echo signal $b_8$ obtained by averaging the latest number Na of echo signals is output from the divider 34.

In the signal processing device of the ultrasonic inspection apparatus arranged as described above, noise components included in each echo signal $b_2$ respectively have different phases, as described above. For this reason, a large number of echo signals are added to each other and averaged, and the noise components are canceled. The noise components as a whole are reduced, and the S/N of flaw echoes included in the echo signals increases, note FIG. 17.

In addition, since a synchronous average with respect to data having the two-side amplitude waveform of an echo signal can be obtained, an effect of reducing noise can be larger than that obtained in a method of synchronously averaging a one-side amplitude signal waveform obtained after an echo signal is detected by an envelope.

In addition, the average number Na of times can be easily changed by properly setting the relationship between the count values $WA_1$ and $RA_1$ of the first write address counter 30a and the first read address counter 30b.

Moreover, when a large number of echo signals are averaged, unexpected large noise can be suppressed. More specifically, an ultrasonic pulse a is incident 1,000 or more times per second. For this reason, as far as visual observation is performed, even if unexpected large noise exceeding a threshold value is input, a person cannot discriminate the noise from the ultrasonic pulse a.

However, in an on-line inspection apparatus, the signal level of an echo signal b is compared with a threshold value every time the ultrasonic pulse a is input, thereby determining the presence/absence of a flaw. For this reason, even if any unexpected noise occurs, the presence of a flaw is decided.

For this reason, when echo signals are averaged, in addition to the level of the above general noise, the level of unexpected noise can be reduced to 1/Na, and the unexpected noise can be prevented from being erroneously determined as a flaw. Therefore, the reliability of the overall apparatus can be more improved.

Figure 16:
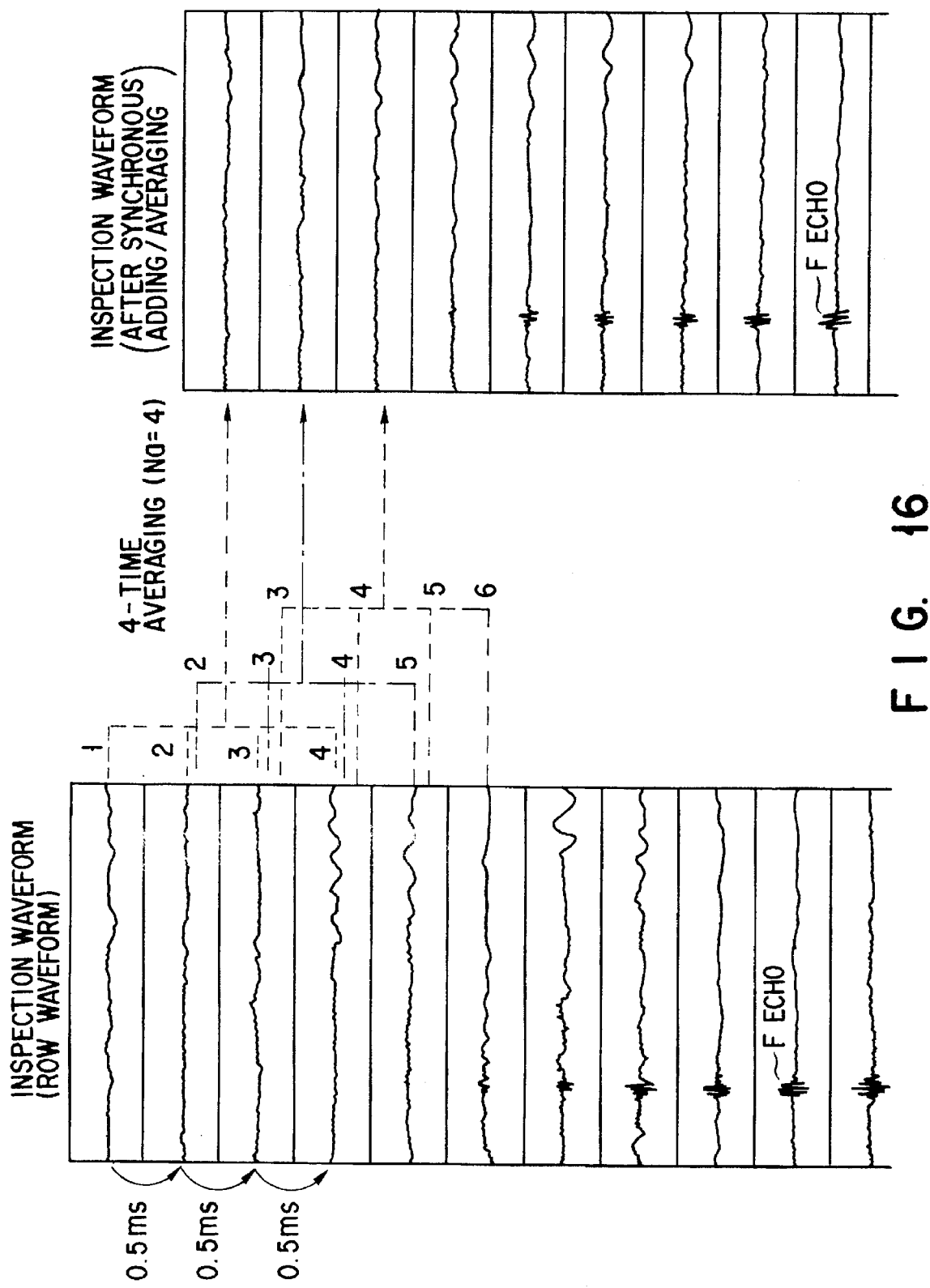
FIG. 16 is a waveform chart of an echo signal showing the effect of the device of the embodiment in FIG. 14.

FIG. 16 is a measured drawing showing comparison between the waveforms of echo signals which are not input to the synchronous adding/averaging circuit 27 and waveforms of echo signals averaged by the synchronous adding/averaging circuit 27 when the average number Na of times is set to be 4. As shown in FIG. 16, it is understood that the S/N of a flaw echo (F echo) in the averaged echo signals is considerably increased.

In addition, the synchronous adding/averaging circuit 27 having the excellent noise reducing function described above can be applied to the device of the embodiment shown in FIG. 1.

More specifically, the digital filter 18 in the device of the embodiment in FIG. 1 can be replaced with the synchronous adding/averaging circuit 27, and the synchronous adding/averaging filter 17 can be omitted.

In this manner, even when the digital filter 18 is replaced with the synchronous adding/averaging circuit 27, a noise component included in an echo signal output from the FIFO register 12 can be considerably reduced.

FIG. 18 is a view showing a main part extracted from a signal processing device of an ultrasonic inspection apparatus according to still another embodiment of the present invention. Note that the same signal processing unit as that of the embodiment shown in FIG. 14 is used as signal processing unit, following an ultrasonic transmit-receive unit 1, for an echo signal b.

In this embodiment, a target object 2a is conveyed, e.g., on a test line in a manufacturing factory at a speed V in a predetermined direction by convey rollers 35a, 35b, 36a, and 36b. A probe 3 is provided by a support mechanism 38 in which water 37 is sealed such that the probe 3 is not in contact with the target object 2a.

In this embodiment, an incident period $T_0$ of ultrasonic pulses a with respect to the target object 2a and a moving speed v of the target object 2a are adjusted, and the ultrasonic pulses a are incident on different positions having 1-mm intervals. Echo signals $b_2$ obtained by the ultrasonic pulses a are averaged by a synchronous adding/averaging circuit 27.

In the signal processing device of the ultrasonic inspection apparatus arranged as described above, Na echo signals $d_2$ sequentially input to the synchronous adding/averaging circuit 27 become echo signals at different positions having 1-mm intervals. Each echo signal b, as shown in FIG. 19, includes a large number of false echoes caused by spreading of a reflected echo (S echo) or bristle echo.

When the incident positions of the ultrasonic pulses a with respect to the target object 2 are slightly changed, each false echo and its phase largely change. Therefore, when a large number of echo signals are added to each other and averaged, false echoes included in the echo signals can be reduced.

Figure 19:
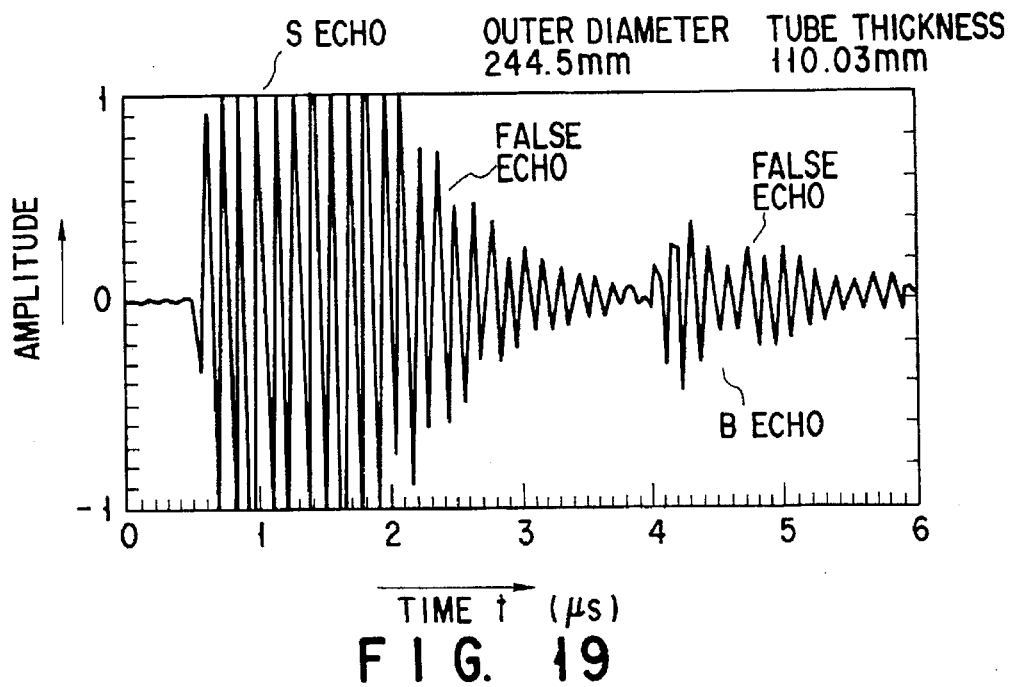
FIG. 19 is a waveform chart of an echo signal including a general reflected echo, a flaw echo, and a false echo.

FIG. 21 is a graph showing an echo signal obtained by averaging echo signals obtained by shifting the incident position of the echo signal shown in FIG. 19 little by little. As shown in FIG. 21, it is understood that false echoes near a surface echo (S echo) and a flaw echo (F echo) are considerably reduced.

Figure 20:
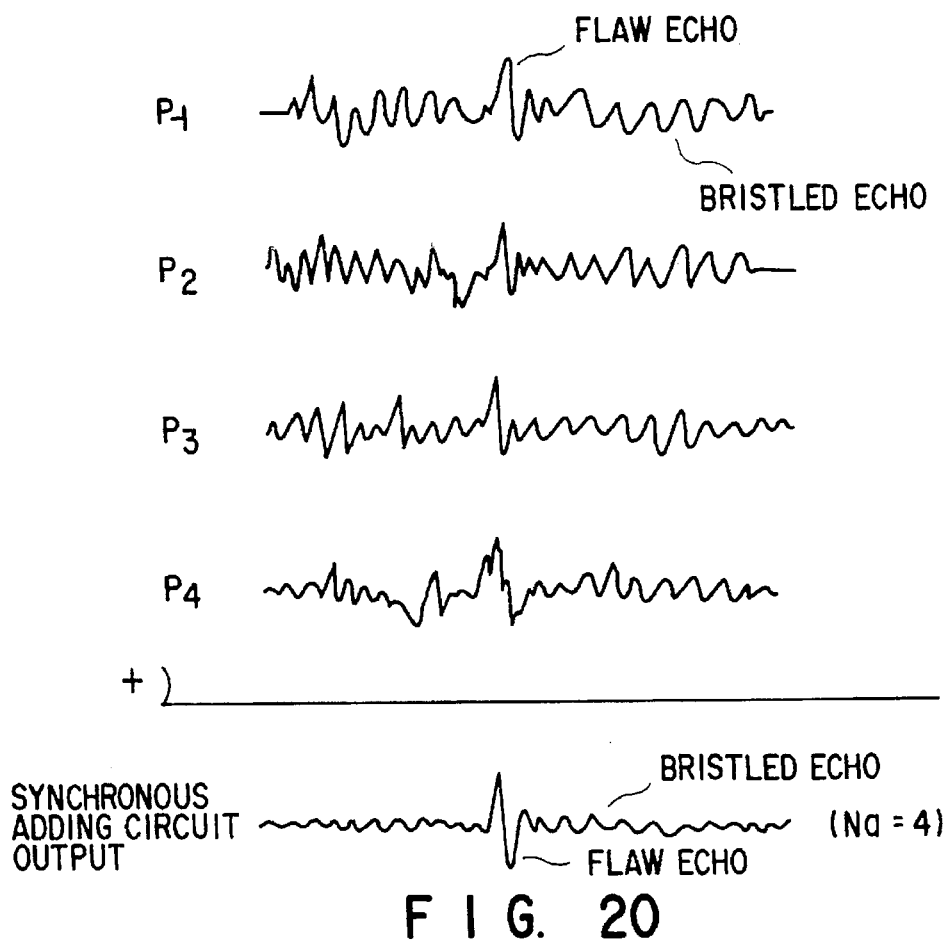
FIG. 20 is a waveform chart of an echo signal showing the operation of the device of the embodiment in FIG. 18.

Assuming that the moving speed V of the target object 2 is set to be 2.5 m/s, that the incident period $T_0$ of the ultrasonic pulse a is set to be 1 ms (frequency f0=1 kHz), and that the average number Na of times is set to be 4, FIG. 20 is a view showing the relationship between the echo signals $b_2$ which are to be input to the synchronous adding/averaging circuit 27 and are located at four positions A/D converter $P_1$, $P_2$, $P_3$, and $P_4$ and one averaged echo signal $b_8$ output from the synchronous adding/averaging circuit 27. It is understood that the level of bristle echo (false echo) located near the flaw echo is considerably lowered.

Figure 22:
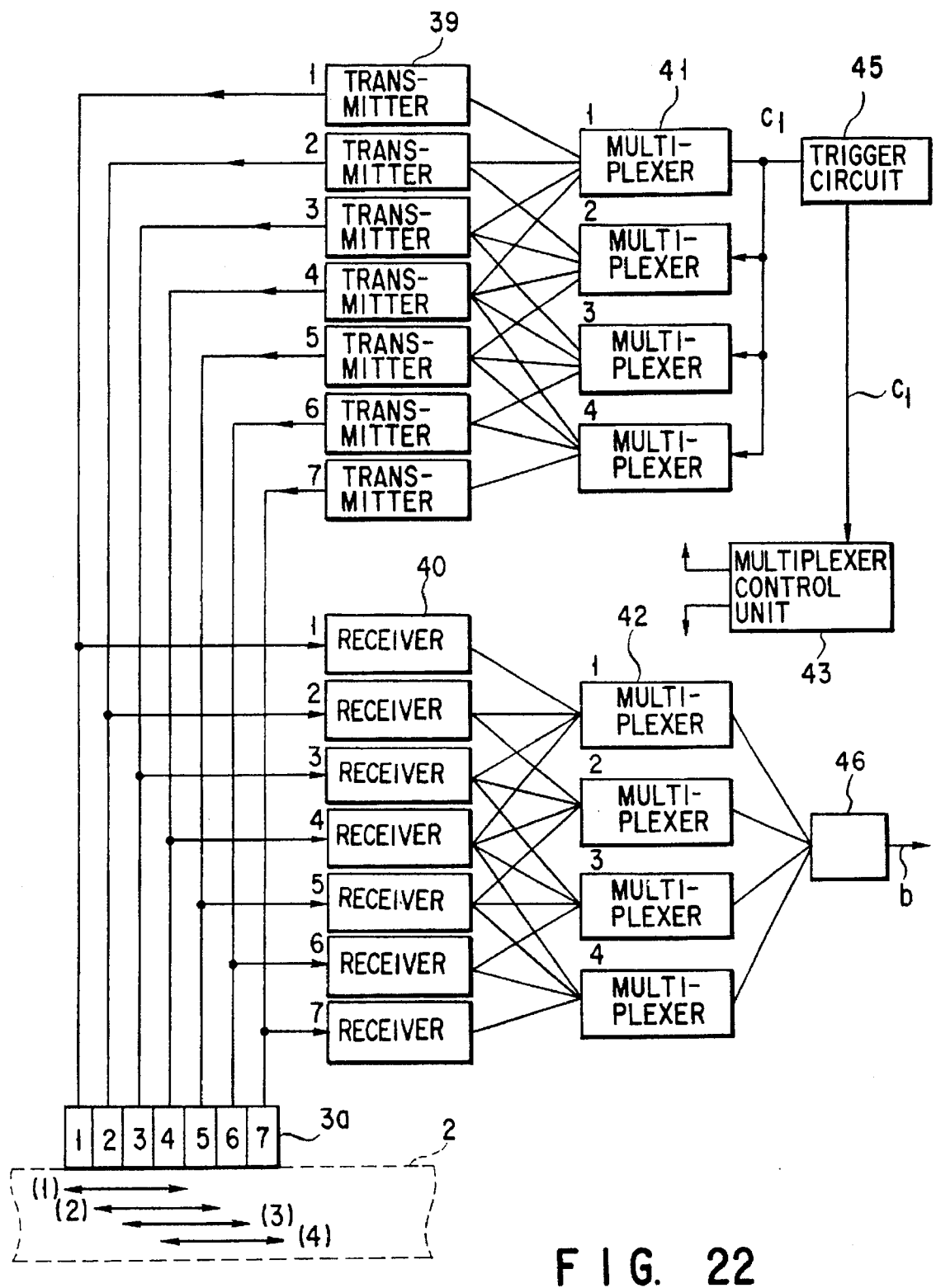
FIG. 22 is a block diagram showing a main part extracted from a signal processing device of still another embodiment.

FIG. 22 is a view showing a main part extracted from a signal processing device of an ultrasonic inspection apparatus according to still another embodiment of the present invention.

In this embodiment, seven probes 3a are arranged in one direction at small intervals, e.g., 1 mm. Note that a plurality of probes arranged in this state are generally called an array probe. A dedicated transmitter 39 applies a pulse signal to each probe 3a. Echo signals output from the seven probes 3a are received by dedicated receivers 40, respectively.

Four multiplexers 41 and four multiplexers 42 are connected to the transmitters 39 and the receivers 40, respectively. Each of multiplexers 41 and 42 is switched and controlled by a multiplexer control unit 43 to which a trigger signal $c_1$ having a period of, e.g., 1 ms and output from a trigger circuit 45 is input. Echo signals output from the multiplexers 42 are synthesized with each other and amplified by an amplifier 46. An echo signal b amplified by the amplifier 46 is input to an A/D converter 11 in FIG. 14. The same signal processing unit as that shown in FIG. 14 is used as a signal processing unit for echo signal processing from the A/D converter 11.

The multiplexer control unit 43 switches and controls the multiplexers 41 and 42 as follows. When a first trigger signal $c_1$ is output from the trigger circuit 45, the first multiplexer 41 selects the first transmitter 39, the second multiplexer 41 selects the second transmitter 39, and the third and fourth multiplexers 41 select the third and fourth transmitter 39, respectively. In addition, the first to fourth multiplexers 42 select the first to fourth receivers 40, respectively.

As a result, first to fourth probes 3a are driven, echo signals from the first to fourth probes 3a are received by the first to fourth multiplexers 42 through the first to fourth receivers 40. Four echo signals output from the first to fourth multiplexers 42 are synthesized with each other, amplified by the amplifier 46, and transmitted to the A/D converter 11 as a new echo signal b.

When a second trigger signal $c_1$ is output from the trigger circuit 45, the first to fourth multiplexers 41 respectively select the second to fifth transmitters 39, and the first to fourth multiplexers 42 respectively select the second to fifth receivers 40. As a result, echo signals b for the second to fifth probes 3a are output from the amplifier 46 in synchronism with the second trigger signal $c_1$.

Similarly, when a third trigger signal $c_1$ is output from the trigger circuit 45, the first to fourth multiplexers 41 respectively select the third to sixth transmitters 39, and the first to fourth multiplexers 42 respectively select the third to sixth receivers 40. As a result, echo signals b for the third to sixth probes 3a are output from the amplifier 46 in synchronism with the third trigger signal $c_1$.

In addition, when a fourth trigger signal $c_1$ is output from the trigger circuit 45, echo signals b for the fourth to seventh probes 3a are output from the amplifier 46.

When a fifth trigger signal $c_1$ is output from the trigger circuit 45, echo signals b for the first to fourth probes 3a are output from the amplifier 46.

More specifically, when the trigger signal $c_1$ is output four times, four types of echo signals b for the probes 3a whose combination changes in turn are output.

The four types of echo signals b have an effect of shifting the incident position of an ultrasonic pulse a as in a case wherein the target object 2 shown in FIG. 18 is substantially moved 1 mm by 1 mm. Therefore, when an average number Na of times in the synchronous adding/averaging circuit 27 is set to be 4, false echoes included in the echo signals can be reduced without actually moving a target object 2.

Note that the combinations of the probes 3a to be selected every trigger signal $c_1$ are not limited to the above combinations [1 to 4], [2 to 5], [3 to 6], and [4 to 7]. For example, when nine probes 3a are used, combinations may be selected as odd- or even-numbered probes like combinations [1357], [2468], and [3579].

FIG. 23 is a block diagram showing the schematic arrangement of a signal processing device of an ultrasonic inspection apparatus according to still another embodiment of the present invention. The same reference numerals as in the embodiment of FIG. 14 denote the same parts in FIG. 23. Therefore, a detailed description of the overlapping parts will be omitted.

In this embodiment, a clock signal d output from a clock signal generation circuit 10 is frequency-divided into an $1/n_1$ clock signal by a frequency divider 47. The frequency-divided clock signal is wave-shaped by a monostable circuit 48 (one-shot multivibrator MU) into a trigger signal c having a small pulse width. The trigger signal c is applied to a delay circuit 13d and an ultrasonic transmit-receive unit 1. The clock signal generation circuit 10, the frequency divider 47, and the monostable circuit 48 constitute a trigger generating means.

In general, the frequency range of an ultrasonic pulse a to be incident on a target object 2 is very wide, i.e., 10 MHz or more. For this reason, in order to satisfy a sampling theorem in the A/D converter 11, a sampling frequency $f_S$ represented by the frequency of the clock signal d must be set to be about 25 MHz. On the other hand, in order to suppress the manufacturing cost of the A/D converter 11, the sampling frequency $f_S$ must be set to be a frequency as low as possible.

However, only when the signal processing device is driven by the clock signal d having a frequency of 25 MHz, as shown in FIG. 24, the clock signal d applied to the A/D converter 11 is not synchronized with the trigger signal c output from the ultrasonic transmit-receive unit 1. For this reason, a sampling timing in the A/D converter 11 varies at a maximum of 40 ns. This variation amount (jitter) means that, in a synchronous adding/averaging circuit 27, as shown in FIG. 24, an offset having a maximum of 40 ns occurs at the sampling position of each data of each echo signal $b_2$.

For example, in an ultrasonic pulse a having a frequency of 10 MHz is used, one period is 100 ns. For this reason, the above variation error of 40 ns almost corresponds to the half wavelength of this period. Therefore, when Na data signal $b_2$ are added to each other and averaged, noise components may not be properly canceled, and an optimal S/N may not be assured.

Therefore, as shown in FIG. 23, a sampling clock signal d is transmitted from one clock signal generation circuit 10 to the A/D converter 11, and, at the same time, the identical clock signal d is frequency-divided and applied to the ultrasonic transmit-receive unit 1 and the delay circuit 13d as the trigger signal c. The ultrasonic transmit-receive unit 1 transmits a pulse signal to a probe 3 in synchronism with this trigger signal c.

Even if a sampling frequency $f_R$ for the A/D converter 11 is low, a generation amount of jitter can be suppressed, noise components included in an echo signal can be reliably canceled, and the S/N of the echo signal can be more increased at low manufacturing cost.

Note that the present invention is not limited to the embodiments described above. In each of the devices of the embodiments, a FIFO register is used as a storing means for storing each sampling data of an A/D-converted echo signal. However, a dual port RAM in which a write terminal and a read terminal are independently provided may be used in place of the FIFO register.

We claim:

1. A signal processing method for an ultrasonic inspection apparatus in which an ultrasonic pulse is transmitted to a target object at a predetermined period, and a flaw present in said target object is detected on the basis of a high-frequency echo signal output from an ultrasonic transmit-receive unit for receiving a reflected wave, comprising the steps of:

converting the echo signal into a digital signal at a predetermined sampling frequency;

designating a measurement time interval in the predetermined period;

sequentially storing, at a write frequency equal to the sampling frequency, sampling data, in the measurement time interval, of the echo signal converted into the digital signal;

sequentially reading out the stored sampling data at a read frequency lower than the write frequency;

performing a frequency discrimination process to the sequentially readout echo signal by a digital filter; and determining the presence/absence of the flaw on the basis of the echo signal to which the frequency discrimination process is performed.

2. A signal processing device for an ultrasonic inspection apparatus in which an ultrasonic pulse is transmitted to a target object at a predetermined period, and a flaw present in said target object is detected on the basis of a high-frequency echo signal output from an ultrasonic transmit-receive unit for receiving a reflected wave, comprising:

A/D converting means for converting the echo signal into a digital signal at a predetermined sampling frequency;

measurement time interval designating means for designating a measurement time interval in the predetermined period;

storing means for sequentially storing, at a write frequency equal to the sampling frequency, sampling data, in the measurement time interval, of the echo signal converted into the digital signal to sequentially output the stored sampling data at a read frequency lower than the write frequency;

a digital filter for performing a frequency discrimination process to the echo signal sequentially output from said storing means; and flaw determining means for determining the presence/absence of the flaw on the basis of the echo signal to which the frequency discrimination process is performed.

3. A signal processing device for an ultrasonic inspection apparatus according to claim 2, wherein said measurement time interval designating means is constituted by a delay circuit for measuring a predetermined delay time from start time of the predetermined period and a write time counter for transmitting a write permission signal to said storing means in only the measurement time interval after measurement of the delay time performed in said delay circuit is ended.

4. A signal processing device for an ultrasonic inspection apparatus according to claim 2, wherein said measurement time interval designating means is constituted by a delay circuit for measuring a set delay time from start time of the predetermined period, a write time counter for transmitting a write permission signal to said storing means in only the measurement time interval after measurement of the delay time which is performed in said delay circuit is ended, and a time setting unit for setting the delay time and the measurement time interval for said delay circuit and said write time counter.

5. A signal processing device for an ultrasonic inspection apparatus according to claim 2, wherein said storing means is a FIFO register.

6. A signal processing device for an ultrasonic inspection apparatus according to claim 2, wherein a synchronous adding/averaging filter for averaging, over a plurality of periods, an echo signal output from the digital filter each time the predetermined period has passed is arranged between said digital filter and said flaw determining means.

7. A signal processing device for an ultrasonic inspection apparatus according to claim 6, wherein said flaw determining means is constituted by D/A converting means for converting an averaged echo signal output from said synchronous adding/averaging filter into an analog signal and comparing means for outputting a flaw signal when a maximum signal level of the averaged echo signal output from said D/A converting means exceeds a predetermined threshold value.

8. A signal processing device for an ultrasonic inspection apparatus in which an ultrasonic pulse is transmitted to a target object at a predetermined period, and a flaw present in said target object is detected on the basis of a high-frequency echo signal output from an ultrasonic transmit-receive unit for receiving a reflected wave, comprising:

A/D converting means for converting the echo signal into a digital signal at a predetermined sampling frequency;

measurement time interval designating means for designating a measurement time interval in the predetermined period;

first storing means for sequentially storing, at a write frequency equal to the sampling frequency, sampling data, in the measurement time interval, of the echo signal converted into the digital signal to sequentially output the stored sampling data at a read frequency lower than the write frequency;

a digital filter for performing a frequency discrimination process to the echo signal sequentially output from said first storing means;

second storing means for sequentially storing data of an echo signal output from said digital filter to sequentially output the stored data at a read frequency equal to the sampling frequency; and D/A converting means for converting an echo signal sequentially output from said second storing means into an analog signal.

9. A signal processing device for an ultrasonic inspection apparatus according to claim 8, characterized in that, after said digital filter temporarily stores all data of the echo signal output from said first storing means, said digital filter performs a frequency discrimination process using all the data, and, upon completion of the process, the digital filter outputs the process result as a digital echo signal.

10. A signal processing device for an ultrasonic inspection apparatus according to claim 8, further comprising flaw determining means for determining the presence/absence of the flaw on the basis of the echo signal converted into the analog signal by said D/A converting means.

11. A signal processing device for an ultrasonic inspection apparatus according to claim 8, wherein said first and second storing means are FIFO registers.

12. A signal processing device for an ultrasonic inspection apparatus in which an ultrasonic pulse is transmitted to a target object at a predetermined period, and a flaw present in said target object is detected on the basis of a high-frequency echo signal output from an ultrasonic transmit-receive unit for receiving a reflected wave, comprising:

A/D converting means for converting the echo signal into a digital signal at a predetermined sampling frequency;

measurement time interval designating means for designating first and second measurement time intervals, which are different from each other, in the predetermined period;

first storing means for sequentially storing, at a write frequency equal to the sampling frequency, sampling data, in the first measurement time interval, of the echo signal converted into the digital signal to sequentially output the stored sampling data at a read frequency lower than the write frequency;

a first digital filter for performing a frequency discrimination process to the echo signal sequentially output from said first storing means;

second storing means for sequentially storing data of an echo signal output from said digital filter to sequentially output the stored data at a read frequency equal to the sampling frequency;

third storing means for sequentially storing, at a write frequency equal to the sampling frequency, sampling data, in the second measurement time interval, of the echo signal converted into the digital signal to sequentially output the stored sampling data at a read frequency lower than the write frequency;

a second digital filter for performing a frequency discrimination process to an echo signal sequentially output from said third storing means;

fourth storing means for sequentially storing data of an echo signal output from said second digital filter to sequentially output the stored data at a read frequency equal to the sampling frequency; and D/A converting means for synthesizing the echo signals output from said second and fourth storing means with each other to convert the echo signals into one analog signal.

13. A signal processing device for an ultrasonic inspection apparatus according to claim 12, further comprising flaw determining means for determining the presence/absence of the flaw on the basis of the echo signal converted into the analog signal by said D/A converting means.

14. A signal processing device for an ultrasonic inspection apparatus according to claim 12, wherein said first, second, third, and fourth storing means are FIFO registers.

15. A signal processing device for an ultrasonic inspection apparatus in which an ultrasonic pulse is transmitted to a target object at a predetermined period, and a flaw present in said target object is detected on the basis of a high-frequency echo signal output from an ultrasonic transmit-receive unit for receiving a reflected wave, comprising:

A/D converting means for converting the echo signal into a digital signal at a predetermined sampling frequency;

measurement time interval designating means for designating a measurement time interval in the predetermined period;

storing means for sequentially storing, at a write frequency equal to the sampling frequency, sampling data, in the measurement time interval, of the echo signal converted into the digital signal to sequentially output the stored sampling data at a read frequency lower than the write frequency;

a synchronous adding/averaging circuit for averaging, over a plurality of periods, an echo signal output from said storing means each time the predetermined period has passed; and flaw determining means for determining the presence/absence of the flaw on the basis of an echo signal output from said synchronous adding/averaging circuit.

16. A signal processing device for an ultrasonic inspection apparatus in which an ultrasonic pulse is transmitted to a target object at a predetermined period, and a flaw present in said target object is detected on the basis of a high-frequency echo signal output from an ultrasonic transmit-receive unit for receiving a reflected wave, comprising:

A/D converting means for converting the echo signal into a digital signal at a predetermined sampling frequency;

measurement time interval designating means for designating a measurement time interval in the predetermined period;

first storing means for sequentially storing, at a write frequency equal to the sampling frequency, sampling data, in the measurement time interval, of the echo signal converted into the digital signal to sequentially output the stored sampling data at a read frequency lower than the write frequency;

a synchronous adding/averaging circuit for averaging, over a plurality of periods, an echo signal output from said first storing means each time the predetermined period has passed;

second storing means for sequentially storing data of an echo signal output from said synchronous adding/averaging circuit to sequentially output the stored data at a read frequency equal to the sampling frequency; and D/A converting means for converting an echo signal sequentially output from said second storing means into an analog signal.

17. A signal processing device for an ultrasonic inspection apparatus according to claim 16, further comprising flaw determining means for determining the presence/absence of the flaw on the basis of the echo signal converted into the analog signal by said D/A converting means.

18. A signal processing device for an ultrasonic inspection apparatus according to claims 15, wherein said synchronous adding/averaging circuit is constituted by a first signal memory for always storing a predetermined number of latest echo signals sequentially output from said storing means, a second signal memory for storing one added echo signal which is added, signal reading means for reading out an echo signal which is written ahead of a latest echo signal in said first memory by a defined number, an adding unit for adding an echo signal sequentially output from said FIFO register to the added echo signal read out from said second signal memory, a subtracting unit for subtracting one echo signal read out by said signal reading means from the added echo signal output from said adding unit, added echo signal updating means for writing, as a new added echo signal, in said second signal memory, the added echo signal output from said subtracting unit, and a dividing unit for dividing the added echo signal output from said subtracting unit to obtain an averaged echo signal.

19. A signal processing device for an ultrasonic inspection apparatus according to claim 15, characterized by further comprising relative shifting means for relatively shifting an incident position of the ultrasonic pulse with respect to said target object.

20. A signal processing device for an ultrasonic inspection apparatus according to claim 15, characterized by further comprising trigger signal generating means for applying, to said ultrasonic transmit-receive unit, a trigger signal synchronized with a sampling timing of said A/D converting means and having a period longer than a sampling period.

21. A signal processing device for an ultrasonic inspection apparatus according to claim 15, wherein said first and second storing means are FIFO registers.

* * * * *

UNITED STATES PATENT AND TRADEMARK OFFICE
CERTIFICATE OF CORRECTION

PATENT NO. : 5,671,154
DATED : September 23, 1997
INVENTOR(S) : IIZUKA et al.

It is certified that error appears in the above-identified patent and that said Letters Patent is hereby corrected as shown below:

Title page, column 2, line 2,
Item [56], "Nusbieckel" should be --Nusbickel--.

Column 22, line 57 (claim 18, line 2),
change "claim 15" to --claim 16--.

Column 23, line 15 (claim 19, line 2),
change "claim 15" to --claim 16--.

Column 24, line 5 (claim 20, line 2),
change "claim 15" to --claim 16--.

Column 24, line 11 (claim 21, line 2),
change "claim 15" to --claim 16--.

Signed and Sealed this

Seventeenth Day of February, 1998

*Attest:*

BRUCE LEHMAN

*Attesting Officer*     *Commissioner of Patents and Trademarks*